(12) United States Patent
Bertelli et al.

(10) Patent No.: US 6,958,218 B2
(45) Date of Patent: Oct. 25, 2005

(54) METHOD FOR THE SCREENING OF $\alpha_2\delta$-1 SUBUNIT BINDING LIGANDS

(75) Inventors: François Bertelli, Royston (GB); Jason Peter Brown, Stapleford (GB); Visaka Udeni Karalliadde Dissanayake, Cambridge (GB); Nirmala Suman-Chauhan, Six Mile Bottom (GB); Nicolas Steven Gee, Dundee (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/090,827

(22) Filed: Mar. 6, 2002

(65) Prior Publication Data

US 2003/0073132 A1 Apr. 17, 2003

Related U.S. Application Data

(63) Continuation of application No. 09/397,549, filed on Sep. 16, 1999, now abandoned.

(51) Int. Cl.⁷ .............................. G01N 33/53; C07K 1/00
(52) U.S. Cl. ......................................... 435/7.1; 530/350
(58) Field of Search ........................... 435/6, 7.2, 7.21, 435/7.93; 530/300, 350; 514/14, 12

(56) References Cited

FOREIGN PATENT DOCUMENTS

| WO | 93/04083 | | 3/1993 |
|---|---|---|---|
| WO | WO 95/04822 | * | 2/1995 |
| WO | 0020450 | | 4/2000 |
| WO | WO 01/20336 | | 3/2001 |

OTHER PUBLICATIONS

Holland et al. A nonseparation microplate receptor binding Assay. Analytical Biochemistry, vol. 222, pp. 516–518.*
Brown and Gee. Cloning and Deletion Mutagenesis of the Alpha 2 beta calcium channel subunit from porcine cerebral cortex. vol. 273, No. 39, pp. 25458–25465, Sep. 1998.*
Gee, N.S., et al., The Journal of Biological Chemistry, The Novel Anticonvulsant Drug, Gabapentin (Neurontin), Binds to the Alpha2Delta Subunit of a Calcium Channel, 1996, vol. 271:10, pp. 5768–5776.
Brown, J.P., et al., The Journal of Biological Chemistry, "Cloning and Deletion Mutagenesis of the Alpha2Delta Calcium Channel Subunit from Porcine Cerebral Cortex", 1998, vol. 273:39, pp. 25458–25465.
Kowalski, M.T., et al. Biochemical Society Transactions, "Effects of Anti–Calcium Channel A2–Subunit Antibodies on Calcium Flux and 1,4–Dihydropyridine Binding" 1990, p. 890.
Gurnett, C.A., et al., The J. of Biological Chemistry, "Extracellular Interaction of the Voltage–Dependent CA2+ Channel Alpha2 Delta and Alpha1 Subunits", 1997, 272:29 PP 18508–18512.
Gurnett, C.A., et al., Neuron, "Dual Function of the Voltage–Dependent CA2+ Channel Alpha2Delta Subunit in Current Stimulation and Subunit Interaction" 1996, vol. 16, PP 431–440.
Felix, R., et al., J. of Neuroscience, "Dissection of Functional Domains of the Voltage–Dependent CA2+ Channel Alpha2Delta Subunit", 1997, vol. 17:18, pp. 6884–6891.
Field, M.J., et al., British Journal of Pharmacology, "Gabapentin (Neurontin) and S–(+)–3–Isobutylgaba Represent a Novel Class of Selective Antihyperalgesic Agents", 1997, vol. 121, pp. 1513–1522.
Klugbauer, N., et al., The Journal of Neuroscience, "Molecular Diversity of the Calcium Channel Alpha2Delta Subunit", 1999, vol. 19:2, pp. 684–691.
Tokumaru, H., et al., European Journal of Pharmacology-Molecular Pharmacology Section, "Purification of the Cardiac 1,4–Dihydropyridine Receptor Using Immunoaffinity Chromatography with a Monoclonal Antibody Against the Alpha2Delta Subunit of the Skeletal Muscle Dihydropyridine Receptor" 1992, vol. 227, pp. 363–370.
Hill, D.R., et al., European Journal of Pharmacology–Molecular Pharmacology Section, "Localization of [3H]Gabapentin to a Novel Site in Rat Brain: Autoradiographic Studies", 1993, vol. 244, pp. 303–309.
Dissanayake, V.U.K., et al., British Journal of Pharmacology, "Spermine Modulation FO Specific [3H]–Gabapentin Binding to the Detergent–Solubilized Porcine Cerebral Cortex Alpha2Delta Calcium Channel Subunit" 1997, vol. 120, pp. 833–840.
Brickley, K., et al., FEBS Letters, "Use of Site–Directed Antibodies to Probe the Topography of the Alpha2 Subunit of Voltage–Gated CA2+ Channels", 1995, vol. 364, pp. 129–133.
Taylor, C.P., et al., Epilepsy Research, Potent and Stereospecific Anticonvulsant Activity of 3–Isobutyl Gaba Relates to in Vitro Binding at a Novel Site Labeled by Tritiated Gabapentin, 1993, vol. 14, pp. 11–15.
Thurlow, R.J., et al., European Journal of Pharmacology-Molecular Pharmacology Section, "[3H]Gabapentin May Label A System–L–Like Neutral Amino Acid Carrier in Brain", 1993, vol. 247, pp. 341–345.
Suman–Chauhan, N., et al., European Journal of Pharmacology–Molecular Pharmacology Section, "Characterisation of [3H]Gabapentin Binding to a Novel Site in Rat Brain: Homogenate Binding Studies", 1993, vol. 244, pp. 293–301.

(Continued)

Primary Examiner—Kenneth R. Horlick
Assistant Examiner—Cynthia Wilder
(74) Attorney, Agent, or Firm—Mehdi Ganjeizadeh; Eric J. Baude; Karen B. King

(57) ABSTRACT

A method for the screening of ligands which bind to soluble $\alpha_2\delta$-1 subtype polypeptides.

3 Claims, 9 Drawing Sheets-

OTHER PUBLICATIONS

Ellis, S.B., et al., Science, "Sequence and Expression of MRNAs Encoding the Alpha1 and Alpha2 Subunit of a DHP–Sensitive Calcium Channel", 1988, vol. 241, pp. 1661–1664.

DeJongh, K.S., The Journal of Biological Chemistry, "Subunits of Purified Calcium Channels", 1990, vol. 265, pp. 14738–14741.

Jay, S.D., et al., The Journal of Biological Chemistry, "Structural Characterization of the Dihydropyridine–Sensitive Calcium Channel Alpha2–Subunit and th eassociated Delta Peptides", 1991, vol. 266, pp. 3287–3293.

Wiser, O., et al., FEBS Letters, The Alpha2/Delta Subunit of Voltage Sensitive CA2+ Channels is a Single Transmembrane Extracellular Protein Which is Involved in Regulated Secretion, 1996, vol. 379, pp. 15–20.

Brown, J.P., et al., Rev. Contemp. Pharmacother, "Mechanisms of Action of Gabapentin", 1996, vol. 7, pp. 203–214.

Brown, J.P., et al., Analytical Biochemistry, "Isolation of the [3H]Gabapentin–Binding Protein/Alpha2Delta CA2+ Channel Subunit from Porcine Brain: Development of a Radioligand Binding Assay for Alpha2Delta Subunits Using [3H]Leucine", 1998, vol. 255, pp. 236–243.

Holland et al., "A Nonseparation Microplate Receptor Binding Assay", *Analytical Biochemistry,* vol. 222, 1994, pp. 516–518.

\* cited by examiner

SPA assay of [$^3$H]gabapentin (18.4nM) binding to s-$\alpha_2\delta$-1b-6His (20µl). Optimisation of Imidazole concentration in the assay.

Flashplate assay of [$^3$H]gabapentin (14nM) binding to s-$\alpha_2\delta$-1b-6His (10μl). Optimisation of Imidazole concentration in the assay.

Flashplate time course of [$^3$H]gabapentin (13nM) binding to various concentrations of s-$\alpha_2\delta$-1b-6His. 10 mM imidazole in assay Determination of s-$\alpha_2\delta$-1b-6His capacity of flashplate assay. Counted after 3hour incubation Determination of the optimum imidazole concentration required to maximize the [$^3$H]gabapentin (13nM) binding window using a constant amount of purified s-$\alpha_2\delta$-1b-6His (2µl). Assayed after 3hour incubation.

Flashplate assay of [$^3$H]gabapentin saturation binding to purified s-$\alpha_2\delta$-1b-6His. Assayed after three hour incubation (see table 1 for details).

Flashplate time course optimisation of Imidazole concentration required to maximize the [$^3$H]Leucine (10.1nM) binding window to s-$\alpha_2\delta$-1b-6His. Assayed after three hour incubation.

Competition curves of three compounds in the flashplate assay format (see table 2 for details). Assayed after 3 hour incubation.

- ■ Gabapentin
- ○ (S+)-3-isobutyl GABA
- ▼ (R-)-3-isobutyl GABA

METHOD FOR THE SCREENING OF α₂δ-1 SUBUNIT BINDING LIGANDS

This application is a continuation of U.S. Ser. No. 09/397,549 filed Sep. 16, 1999; now abandoned the entire contents of which are herein incorporated by reference.

FIELD OF THE INVENTION

The invention relates to a method for the screening of ligands which bind a soluble secreted cerebral cortical voltage-dependent calcium channel α₂δ-1 subunit polypeptide.

BACKGROUND OF THE INVENTION

Gabapentin (1-aminoethyl-cyclohexane acetic acid) is currently commercialized for the treatment of epilepsy. The compound has however been recognized as being also useful for the treatment of pain and anxiety.

Recent reports have suggested an interaction between gabapentin and the α₂δ subunit of a voltage-dependent calcium channel (VDCC). But electro-physiological studies have yielded conflicting data on the action of gabapentin at VDCCs, even though the relevance of the interaction of gabapentin at the α₂δ subunit to the clinical utility of the drug is becoming clearer. However, none of the prototype anticonvulsant drugs displace [³H]gabapentin binding from the α₂δ-1 subunit.

The most frequently used assay currently available for the screening of ligands that bind the α₂δ subunit involves the use of pig membrane extracts as a source of the α₂δ subunit. Such an assay presents major inconvenience. Firstly, because the assay material is a membrane extract, it is very difficult to accurately determine the protein composition from one assay preparation to another particularly with regard to the subtype. Also, the presence of various impurities in the assay preparation is a problem in small plate assays. Furthermore, as the protein preparation lacks homogeneity, the interaction between the targeted protein and the assay plate is often quite uneven. This renders the streamlining of the assay in a high throughput format almost impossible to achieve.

SUMMARY OF THE INVENTION

The inventors have found that it was possible to use a soluble secreted form of a voltage-dependant calcium channel α₂δ-1 subunit polypeptide (hereinafter α₂δ-1 subunit polypeptide) in an assay for the screening of ligands which bind the α₂δ-1 subunit.

The exact position and configuration of the [³H] gabapentin binding site on the α₂δ subunit is not currently known. Furthermore, recent deletion experiments on the porcine α₂δ-1 subunit coding sequence have shown that amino-acids close to the C-terminal region are needed in order for the protein to bind [³H]gabapentin. For this very reason, the use of truncated forms of the porcine α₂δ-1 subunit in screening assays has not been disclosed or suggested in the prior art because there was concern as to whether relevant levels of binding capacity would be achieved in an assay environment.

The assay of the invention is of considerable interest because it confirms that a recombinant soluble secreted α₂δ-1 subunit polypeptide can be used in high throughput α₂δ-1 ligand screening. It also provides a useful advantage over the pig membrane extract screening assay as it allows the study of α₂δ-1 subtype-specific binding ligands. Proteins can be tagged which makes purifying convenient and possible to use a tagged antibody for recognition.

It was not clear whether the addition of the 6His tag to the C-terminus of the protein would affect the [³H]gabapentin binding properties of α₂δ

It was also unclear whether a C-terminally located 6His tag on α₂δ would be accessible for interaction with the Ni NTA chromatography matrix (for purification purposes) and SPA bead, or Ni flashplate well surface (for purposes of the assay).

The invention concerns a method for the screening of ligands which bind a calcium channel α₂δ-1 subunit.

The method comprises the steps of:
contacting a secreted soluble recombinant calcium channel α₂δ-1 subunit polypeptide with:
  a ligand of interest; and
  a labelled compound which binds a α₂δ-1 subunit; and
measuring the level of binding of the labelled compound to the secreted soluble α₂δ-1 subunit.

The invention also concerns a kit for the screening of ligands which bind a calcium channel α₂δ-1 subunit.

The kit comprises:
a secreted soluble recombinant calcium channel α₂δ-1 subunit polypeptide; and
a labelled compound which binds a calcium channel α₂δ-1 subunit.

DETAILED DESCRIPTION OF THE INVENTION

Figure 1:
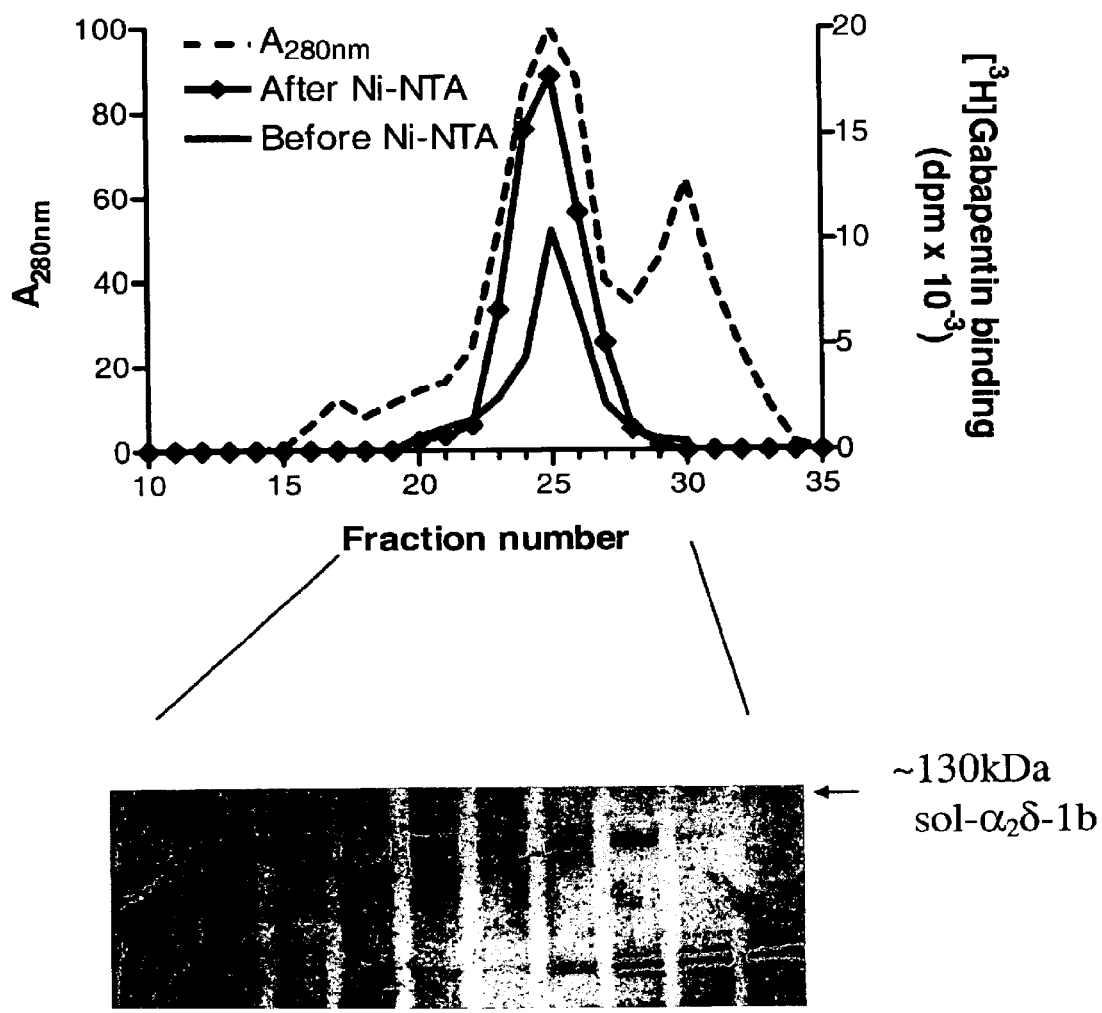
FIG. 1 represents the elution profile of the recombinant polypeptide with the amino acid sequence of SEQ ID NO:9 purified by Superdex-200 chromatography, either before or after electron on NI-NTA.

The invention concerns a method for the screening of ligands which bind a soluble secreted α₂δ-1 subunit polypeptide. The term $\alpha_2\delta$-1 subunit polypeptide, when used herein, is intended to designate a structure containing two polypeptides ($\alpha_2$ and $\delta$) attached to one another by covalent desulfide bridges. More particularly, the targeted $\alpha_2\delta$-1 subunit binding site is preferably the [$^3$H]gabapentin binding site. The various parameters of the method of the invention are described in further detail below.

A—Secreted Soluble Recombinant $\alpha_2\delta$-1 Subunit Polypeptide

Several nucleotide sequences encoding a secreted soluble form of an $\alpha_2\delta$-1 subunit can be used in the context of the present invention. Preferred soluble secreted $\alpha_2\delta$-1 subunit polypeptides are derived from eukaryotic $\alpha_2\delta$-1 subunits, more preferably from mammal, such as mouse, rat, rabbit, porcine, bovine or others and human $\alpha_2\delta$-1 subunits. Most preferred soluble secreted $\alpha_2\delta$-1 subunit polypeptides are derived from the human or porcine $\alpha_2\delta$-1 subunits.

More specifically, the selected nucleotide sequences encode a secreted soluble polypeptide having at least 80%, preferably 90%, more preferably 95%, and most preferably 98 or 99% amino-acid identity with the polypeptide comprising from amino acid 1 to between amino-acids 985 and 1054, preferably between amino-acids 985 and 1059, and most preferably between amino-acids 1019 and 1044 of SEQ ID NO: 5 or SEQ ID NO: 16.

In order to determine the optimal deletions on the $\alpha_2\delta$-1 subunit cDNA that yield a soluble secreted polypeptide devoid of membrane anchorage structures and having a functional [$^31$H]gabapentin binding site, the inventors tested the expression of several human or porcine $\alpha_2\delta$-1 subunit cDNA deletion mutants. The discussion provided below provides detailed comments on possible truncations, giving as an example the porcine $\alpha_2\delta$-1 subunit. However, given the very substantial cross-species homology for $\alpha_2\delta$-1 subunit sequences, the comments below can also be applied o other eukaryotic species, and more particularly other mammation species such as the rat, the mouse or the rabbit. Their $\alpha_2\delta$-1 subunit sequences, which are available in public databases, share a very substantial homology with the human and porcine $\alpha_2\delta$-1 subunit sequences.

The inventors found that by deleting from the porcine $\alpha_2\delta$-1 subunit cDNA a nucleotide sequence encoding as much as amino-acids 967 to 1091 of the native protein, soluble polypeptides could be obtained. On the other hand, the minimal deletion required to achieve solubility appears to be located around nucleotides encoding amino-acids 1064 to 1091 of the sequence of SEQ ID NO: 5. In this regard, the mutant polypeptide expressed using a cDNA deletion mutant from which a sequence encoding amino-acids 1064 to 1091 is removed is found in both soluble and membrane-associated forms, with [$^3$H]gabapentin and/or other derivatives or compounds such as pregabalin and gabapentoids binding properties similar to that of the wild type protein. Furthermore, a mutant protein expressed using a cDNA deletion mutant from which a nucleotide sequence encoding amino-acids 1085 to 1091 is removed recovers its membrane anchorage properties. Also, mutant proteins expressed using cDNA deletion mutants from which nucleotide sequences encoding either amino-acids 1037 to 1091 or amino-acids 1019 to 1091 of SEQ ID NO: 5 or 16 are removed are found in soluble form.

The inventors believe that the soluble secreted $\alpha_2\delta$-1 subunit polypeptides which are as close as possible to the native sequence and which are therefore more likely to retain their native folding and hence their [$^3$H]gabapentin-binding properties are those corresponding to a protein in which amino-acid stretch 985–1091 to 1074–1091, the amino-acid sequence of SEQ ID NO: 5 or 16 has been deleted. The skilled scientist can quite easily determine within this amino-acid stretch the optimal mutant protein.

The invention therefore particularly concerns a screening assay in which the secreted soluble $\alpha_2\delta$-1 subunit polypeptide is preferably a polypeptide having at least 80% identity with the polypeptide comprising from amino-acid 1 to between amino-acid 985 and 1054, preferably between amino-acids 985 and 1059, and most preferably between amino-acids 1019 and 1064 of SEQ ID NO:5 or SEQ ID NO:16. Preferred $\alpha_2\delta$-1 subunit polypeptides which can be used in the present invention are those of SEQ ID NO:6, 7, 8, 9, 13, 14 and 15, with the polypeptides of SEQ ID NO:9 or SEQ ID NO:15 being most preferred.

In a first and preferred embodiment of the invention, the $\alpha_2\delta$-1 subunit polypeptide is purified before it is used in the assay. The purification step, an example of which is provided further in this specification, can be carried out using several purification techniques well-known to the skilled person.

In some instances, it is required to tag the $\alpha_2\delta$-1 subunit polypeptide prior to purification. The tag is then in most instances encoded into the nucleotide sequence that is needed to express the polypeptide. Examples of such tags include, but are not limited to sequences encoding C-myc, FLAG, a sequence of histidine residues, heamaglutin A, V5, Xpress or GST. Most of these tags can be incorporated directly into the sequence, for instance through PCR amplification by incorporating the appropriate coding sequence in one of the PCR amplification primers. However, the tag can also be introduced by other means such as covalent binding of the appropriate nucleic acid sequence encoding the tag moiety with the 5' or 3' end of the nucleic acid sequence encoding the polypeptide sequence. This is the case for GST. It should be noted that the tag can be located at either end of the polypeptide sequence. Furthermore, in some instances, it can be advantageous to insert a cleavage site between the tag and the polypeptide sequence in order to permit removal of the tag sequence if needed.

In other cases, providing a tag to the polypeptide is not needed. For instance, the protein can be purified using affinity columns loaded with specific monoclonal antibodies.

In a second embodiment of the invention, the $\alpha_2\delta$-1 subunit polypeptide can be only partially purified. For instance, it can be purified along with other contaminating proteins using an appropriate chromatography matrix such as ion-exchange chromatography column. In such instances, it is not required to tag the desired polypeptide of interest.

The most preferred embodiment contemplated by the inventors concerns the use of a purified tagged $\alpha_2\delta$-1 subunit polypeptide. A particularly preferred tag is a nucleotide sequence encoding from 2 to 10, and preferably 6 histidine residues as provided in the polypeptide of SEQ ID NO:9.

With regard to the $\alpha_2\delta$-1 subunit polypeptide used subsequently in the screening assay of the invention, several possibilities are also open to the skilled person.

In a first and preferred embodiment, the $\alpha_2\delta$-1 subunit polypeptide comprises a tag moiety which can be selected among the tags referred to above. Such tagged polypeptides are particularly useful in SPA or flashplate assays. A preferred tag is the nucleotide sequence encoding histidine residues referred to above.

In a second embodiment, the $\alpha_2\delta$-1 subunit polypeptide can be used without a tag. This is the case for instance in SPA or flashplate assays comprising beads or plates coated with wheat germ lectin. In such an embodiment, the tag is not needed as the carbohydrate moieties of the $\alpha_2\delta$-1 subunit polypeptide bind directly to the wheat germ lectin-coated beads or plates.

B—Labelled Compounds Which Bind the $\alpha_2\delta$-1 Subunit Polypeptide

In cases where the $\alpha_2\delta$-1 binding site is the [$^3$H] gabapentin binding site, the preferred labelled compound which can be used is of course gabapentin itself. However, gabapentin is not the only labelled compound which can be used in this context. Indeed, it has been previously demonstrated that saturation binding analyses on porcine synaptic plasma cerebral cortex membranes performed in the presence of L-leucine indicate a competitive interaction of the amino acid with the [$^3$H]gabapentin binding site, significantly reducing [$^3$H]gabapentin binding affinity for the site. The inventors believe that this competitive interaction is true across across all the amino-acids listed in table 1 below.

TABLE 1

Binding affinities of selected amino acids ($IC_{50}$ < 500 nM) for the [$^3$H]gabapentin site in porcine cortical membranes

| COMPOUND | $IC_{50}$ (NM) ARITHMETIC MEAN (N = 3) ± S.E.M. |
|---|---|
| Gabapentin | 42.1 ± 5.5 |
| L-Norleucine | 23.6 ± 6.7 |
| L-Allo-Isoleucine | 32.8 ± 6.0 |
| L-Methionine | 49.6 ± 10.0 |
| L-Leucine | 61.3 ± 20.9 |
| L-Isoleucine | 68.8 ± 1.9 |
| L-Valine | 330 ± 18 |
| L-Phenylalanine | 351 ± 89 |

It is therefore possible to use commercially available labelled forms of these high affinity ligands in replacement of gabapentin. The utility of [$^3$H]L-leucine has been demonstrated in a filter binding assay and in a flashplate assay format. The inventors believe that labelled amino acids but also other compounds, with affinities preferably below 500 nM in the binding assay can be used as replacements of gabapentin.

With regard to the label, several embodiments can be used in the context of the invention. Preferred labels are of course radioactive labels, a list of which is provided further in this specification.

C—Assay Formats and Conditions

Several assay formats can be used to carry out the method of the present invention. Preferred assay formats include scintillation assays such as the scintillation proximity assay (SPA) or the flashplate assay. Other assay formats well known to those skilled in the arts such as the filter binding assay and the centrifugation assay are also contemplated in the present invention.

SPA and flashplate assays are preferred assay formats for the present invention. Additional details on these assays are provided below.

Scintillation Assay Format

Scintillation assays technology either involves the use of scintillant beads (for the SPA assay) or plates (for the flashplate assay). SPA beads are usually made from either cerium-doped yttrium ion silicate (y2SiO5:Ce) or polyvinyltoluene (PVT) containing an organic scintillant such as PPO. Flashplates commonly used are those such as Ni chelate flashplates although other flashplates can also be used.

Assays are usually carried out in aqueous buffers using radioisotopes such as $^3$H, $^{125}$I, $^{14}$c, $^{35}$S or $^{33}$P that emit low-energy radiation, the energy of which is easily dissipated in an aqueous environment. For example, the electrons emitted by $^3$H have an average energy of only 6 keV and have a very short path length (–1 ~tm) in water. If a molecule labelled with one of these isotopes is bound to the bead or flashplate surface, either directly or via interaction with another molecule previously coupled to the bead or flashplate, the emitted radiation will activate the scintillant and produce light. The amount of light produced, which is proportional to the amount of labelled molecules bound to the beads, can be measured conveniently with a liquid scintillation (LS) counter. If the labelled molecule is not attached to the bead or a flashplate surface, its radiation energy is absorbed by the surrounding aqueous solvent before it reaches the bead, and no light is produced. Thus, bound ligands give a scintillation signal, but free ligands do not, and the need for a time-consuming separation step, characteristic of conventional radioligand binding assays, is eliminated. The manipulations required in the assays are reduced to a few simple pipetting steps leading to better precision and reproducibility.

The conditions under which SPA and flashplate assays are performed in the context of the present invention are provided below.

Scintillation Assay Conditions

1) SPA Assay

The SPA assays is first developed to optimize the conditions under which the radioligand binds the $\alpha_2\delta$-1 subunit polypeptide. The parameters which can be varied to optimize radioligand binding in a typical SPA assay using Amersham beads include assay temperature, $\alpha_2\delta$-1 subunit polypeptide interaction with the radioligand and the SPA beads, radioligand concentration as well as pH variations.

The temperature at which the assay can be carried out can vary from 1 to 30° C. Preferred temperatures range from 18 to 23° C., with 21° C. being the most preferred temperature. The interaction of the $\alpha_2\delta$-1 subunit polypeptide with the SPA beads can be optimized by adjusting the concentration of the polypeptide with SPA beads can be optimized by favor this interaction. When 50 mg of Amersham SPA beads are used, the $\alpha_2\delta$-1 subunit polypeptide concentration may vary from 0.1 to 10 pmoles per well, with the optimal concentration being generally around 5 to 6 pmoles per well.

As for the reagent favoring the interaction between the $\alpha_2\delta$-1 subunit polypeptide and the radioligand as well as the Amersham SPA beads, the inventors found that imidazole could be efficiently used for that purpose when the $\alpha_2\delta$-1 subunit polypeptide is tagged with an amino acid sequence including 6 histidine residues. Furthermore, and more importantly, it was found that imidazole also enhanced binding of the radioligand to the $\alpha_2\delta$-1 polypeptide.

The optimal concentration of imidazole used to enhance radioligand binding varies depending on the concentration of $\alpha_2\delta$-1 subunit polypeptide used in the assay. For instance, when the concentration of the $\alpha_2\delta$-1 subunit polypeptide is about 20 µl ($\alpha_2\delta$-1 polypeptide concentration of 0.6 pmol/ul), imidazole concentrations ranging from 10 to 50 mM can be used, with concentrations ranging between 10 and 30 mM being preferred. A most preferred imidazole concentration is 20 mM. It is to be noted that other compounds such as histidine can be used to enhance radioligand binding. Furthermore, pH variations can also influence radioligand binding although pH variations should be closely monitored as they may have an effect on the structural configuration of the of $\alpha_2\delta$-1 subunit polypeptide. Also the use of imidazole is preferred to enhance radioligand binding, the person skilled in the art know that the use of imidazole is preferred but is absolutely not essential.

The concentration of the radioligand is evaluated with respect to the concentration of $\alpha_2\delta$-1 subunit polypeptide present in the assay medium. Generally, the concentration of radioligand varies from 1 nM to 100 nM. A preferred [$^3$H]gabapentin concentration is about 5 to 20 nM, with a most preferred concentration being about 10 nM. A preferred [$^3$H]leucine concentration is also about 5 to 20 mM, with a most preferred concentration being about 10 nM. It is to be noted that the concentration of other radioligands having affinities similar to those of [$^3$H]gabapentin and [$^3$H]leucine should also be in the range of about 5 to 20 nM.

Once the optimal radioligand binding conditions have been determined, a test ligand can be introduced in the assay medium to evaluate the level of displacement of the radioligand. The concentration of test ligand to be introduced in the assay medium usually varies from 0.1 nM to about 100 µM. A preferred test ligand concentration of about 10 µM is usually a starting point in a high throughput screening assay. Then, depending on the number of hits obtained, it may be lowered or increased.

It is to be noted that the parameters set forth above, which have been evaluated for a typical SPA assay using Amersham SPA beads can be adjusted by the skilled person, for example if SPA beads of a different type are used.

2) Flashplate Assay

Similarly to the SPA assays, the flashplate can first be developed in order to optimize the conditions under which the radioligand binds the $\alpha_2\delta$-1 subunit polypeptide. The parameters which can be varied to optimize radioligand binding in a typical flashplate assay using NEN Ni chelate flashplates also include assay temperature, $\alpha_2\delta$-1 subunit polypeptide interaction with both the radioligand and the flashplates, radioligand concentration as well as pH variations.

The temperature at which the assay can be carried out can vary from 1 to 30° C. Preferred temperatures range from 18 to 23° C., with 21° C. being the most preferred temperature.

The interaction of the $\alpha_2\delta$-1 subunit polypeptide with the flashplates can be optimized by adjusting the concentration of the polypeptide and by introducing a reagent which will favor this interaction. When a standard NEN Ni chelate flashplate is used, the $\alpha_2\delta$-1 subunit polypeptide volume usually varies between 0.5 and 20 µl for a concentration of $\alpha_2\delta$-1 subunit polypeptide of 0.6 pmol/µl. As the published maximum binding capacity of NEN plates is about 6 pmol per well, the inventors consider that an optimal concentration of $\alpha_2\delta$-1 subunit polypeptide is probably around 5 pmol per well at 8 µl.

Also the use of imidazole is preferred to enhance radioligand binding, the person skilled in the art know that the use of imidazole is preferred but is absolutely not essential.

With regard to the reagent favoring the interaction between the $\alpha_2\delta$-1 subunit polypeptide and the radioligand as well as the flashplates, the inventors found that imidazole could also be efficiently used for that purpose when the $\alpha_2\delta$-1 subunit polypeptide is tagged with an amino acid sequence including 6 histidine residues. It was also found that imidazole concentrations substantially enhanced binding of the radioligand to the $\alpha_2\delta$-1 polypeptide. The optimal concentration of imidazole used to enhance radioligand binding varies depending on the concentration of $\alpha_2\delta$-1 subunit polypeptide used in the assay. For instance, when the volume of the $\alpha_2\delta$-1 subunit polypeptide is about 10 µl µl ($\alpha_2\delta$-1 polypeptide concentration of 0.6 pmol/ul), the optimal imidazole concentration can vary between 1 and 20 mM, with a concentration of about 10 mM being preferred. As mentioned previously, other compounds such as histidine as well as pH variations may be used to enhance radioligand binding.

The concentration of the radioligand is evaluated with respect to the concentration of $\alpha_2\delta$-1 subunit polypeptide present in the assay medium. Generally, the concentration of radioligand varies from 1 nM to 100 nM. A preferred [$^3$H]gabapentin concentration is about 5 to 20 nM, with a most preferred concentration being about 10 nM. A preferred [$^3$H]leucine concentration is also about 5 to 20 nM, with a most preferred concentration being about 10 nM. It is to be noted that the concentration of other radioligands having affinities similar to those of [$^3$H]gabapentin and [$^3$H]leucine should also be in the range of about 5 to 20 nM.

Once the optimal radioligand binding conditions have been determined, a test ligand can be introduced in the assay medium to evaluate the level of displacement of the radioligand. The concentration of test ligand to be introduced in the assay medium usually varies from 0.1 nM to about 100 µM. A preferred test ligand concentration of about 10 µM is usually a starting point in a high throughput screening assay. Then, depending on the number of hits obtained, it may be lowered or increased.

The inventors have tested the displacement of a particular radioligand, [$^3$H]gabapentin, with (S+)-3-isobutyl gaba, (R–)-3-isobutyl gaba and gabapentin. The data provided in the examples which follow clearly shows that the assay can be used in high throughput competition studies.

EXAMPLE 1

Construction of a Nucleotide Sequence Encoding the Putative Soluble Porcine $\alpha_2\delta$-1b Deletion Mutant of SEQ ID NO: 9 a) Primer Design

PCR primers were designed to generate the soluble porcine $\alpha_2\delta$-1*b* deletion mutant of SEQ ID NO: 9 as follows:

5' PCR primer: This was designed to engineer in a KOZAK translation initiation consensus sequence prior to the coding sequence (Kozak *JBC* 266 19867–19870)

3' PCR primer: This was designed to engineer in six histidine residues followed by a stop-codon at the desired location in the coding sequence. In addition to the stop codon the $\alpha\delta$-1 primers also included an Eco RI restriction site.

The bold region in each primer sequence denotes the 'tagged' region; addition of sequences not present in the template. Primers were custom synthesized by Perkin Elmer Applied Biosystems UK to the ABI ready pure grade, supplied lyophilized then resuspended to 15 µM in 10 mM TE. JB189 and 195 were provided without 5' phosphate groups:

```
5' primer JB189  (5'-TCGCCACCATGGCTGCTGGCTGCCTGCTG-3',                         SEQ ID NO:20)

3' primer JB195  (5'-TCGGAATTCCTCAGTGATGGTGATGGTGATGAGAAACACCACCACAGTCGGT-3',  SEQ ID NO:21)
``` b) PCR Protocols for the Generation of the $\alpha_2\delta$-1 Deletion Mutant

1) Generation of the PcDNA3-Porcine-$\alpha_2\delta$-1-(+) PCR Template

An oligo dT-primed λgt10 porcine cerebral cortical cDNA library was screened by ECL (Amersham) using a 2,381-bp HindIII fragment (coding sequence 268–2649) of the rabbit skeletal muscle $\alpha_2\delta$ clone (pcDNA3-Rab-$\alpha_2\delta$-(+)) (supplied by Neurex) as the probe.

A positive insert was identified and subcloned into pBluescript-SK-(+) to generate pB-PC-$\alpha_2\delta$-1.1. The clone was sequenced on both strands, except for a 711-bp stretch at one end of the clone, which had a high degree of homology to mitochondrial C oxidase.

The $\alpha_2\delta$ coding region was homologous to the 3' region of the human neuronal $\alpha_2\delta$ sequence but lacked 926 bp of 5' coding sequence. The missing sequence was obtained by 5'-RACE using total RNA prepared from porcine cerebral cortex. RACE was performed across a Bgl I site unique in known $\alpha_2\delta$ sequences (rabbit (accession no. M21948)), rat (accession number M86621), human (accession no. M76559).

The sequence derived from the 5' RACE product was used to design a primer (JB042, 5'-GGGGATTGATCTTCGATCGCG-3'; SEQ ID NO: 18) specific for the 5'-untranslated end of the cDNA. PCR was then performed with Pfu DNA polymerase using JB042 and a primer downstream of the Bgl I site (JB040, CTGAGATTTGGGGTTCTTTGG, SEQ ID NO: 19).

The PCR product was ligated to Eco RI linkers (5'-GGAATTCC-3') and then digested with Eco RI and Bgl I. The 1,564-bp fragment (5' portion of the $\alpha_2\delta$ cDNA) was gel-purified.

Similarly, a 2,303-bp fragment (3' portion of the $\alpha_2\delta$ cDNA) was isolated after digestion of pB-PC-$\alpha_2\delta$-1.1 with Bgl I and Eco RI. The two fragments of $\alpha_2\delta$ cDNA were then ligated to EcoRI-digested pcDNA3 in a three-way ligation. A clone was picked with the full-length $\alpha_2\delta$ sequence in the positive orientation with respect to the cytomegalovirus promoter (pcDNA3-PC-$\alpha_2\delta$-(+)).

2) PCR Protocol

The following reagents were added to obtain two cocktails labelled 'lower' and 'upper' buffers.

|  | μl |
|---|---|
| Lower |  |
| 10x Pfu DNA polymerase buffer | 25 |
| 10 mM dNTP's | 5 |
| 100 ng/μl pcDNA3-porcine-$\alpha_2\delta$-(+) | 10 |
| 15 μM JB189 | 8.5 |
| 15 μM JB195 | 8.5 |
| $H_2O$ | 193 |
| Upper |  |
| 10x Pfu DNA polymerase buffer | 25 |
| $H_2O$ | 220 |
| 2.5 units/μl Pfu DNA polymerase | 5 |

50 μl aliquots of lower buffer were added to each of four 0.5 ml eppendorf tubes. To each was added one PCRgem 100 ampliwax bead (PE biosystems). Tubes were heated to 80° C. for 2 minutes then cooled to 4° C. 50 μl of upper buffer was then added to each tube. Tubes were then cycled on a Stratagene Robo-Cycler according to the following conditions: 98° C./1 min 30 sec, followed by: for 20 cycles 98° C./45 sec, 54° C./2 min, 72° C./6 min, followed by: 72° C./20 min, followed by: hold at 4° C.

The 3228 bp PCR product was then purified on a QIAquick PCR purification column (Qiagen) and eluted with 61 μl of $H_2O$. The following reagents were added to the eluted DNA: 0.7 μl 10 mM ATP, 7 μl 10× Polynucleotide Kinase buffer, 1 μl 1 unit/μl Polynucleotide Kinase.

The above 5' phosphorylation reaction was incubated at 37° C. for 1 hour. The reaction was stopped by incubation at 65° C. for 10 min. The 3228 bp 5' phosphorylated PCR product was then gel purified from a 1% agarose gel using QIAEX (Qiagen) beads and eluted in ~50 μl.

EXAMPLE 2

Cloning of the PCR Fragments of Example 1 into the Baculovirus Transfer Vector pFastBac1

The PCR products of Example 1 (3228 bp JB189/JB195 derived PCR product coding for 6His tagged porcine $\alpha_2\delta$-1b: SEQ ID NO:9) were cloned into Stu I digested, calf intestinal phosphatase dephosphorylated, phenol chloroform extracted and QIAEX gel purified pFastBac1 (Life Technologies) using the Rapid DNA ligation kit (Roche Diagnostics) transforming XL1-blue ($\alpha_2\delta$-1b) E. Coli cells:

a) Screening for Positive Recombinants

Given that the PCR product was cloned by blunt-end ligation a screen was required to select a recombinant with the gene ligated in the positive orientation with respect to the polyhedrin promoter in pFastBac1. This was achieved by restriction digest of miniprep DNA (Qiagen miniprep kit) prepared from colony minicultures and analysis on a 1% TAE

| SEQ ID NO:9 in pFastBac1 Eco RI digest performed on miniprep DNA | |
|---|---|
|  | Predicted fragments (bp) |
| PCR product cloned in a positive orientation | 4773 and 3230 |
| PCR product cloned in a negative orientation | 7989 and 14 | b) Sequencing Analysis of Selected Clones

One positive was selected for this clone and used to prepare a plasmid DNA stock of the desired construct (QIAGEN maxi kit). Confirmatory sequence reactions were performed using the Big Dye terminator sequencing kit and run on an ABI 310 Prism Genetic Analyzer. Sequence analysis of both coding strands was performed using a selection of sequencing oligonucleotide primers and has yielded the following results:

Sequencing of pFBac-Porcine-s-$\alpha_2\delta$-1-$\Delta$1040–1067-6His confirmed that the insert sequence corresponded to tbe nucleic acid encoding the polypeptide of SEQ ID NO:9, except for the deletion of two bases from the 5' end of the 5' PCR primer (JB189). The loss of these two bases did not have any impact on the 5' end of the gene as the KOZAK translation start-site consensus (GCCACC) starts immediately after this deletion.

EXAMPLE 3

Protocol for Establishing Baculovirus Banks for the Expression of the $\alpha_2\delta$-1 Deletion Mutant of SEQ ID NO: 9

Essentially, the protocol used to generate the baculovirus banks is that outlined in the Life Technologies Bac-to Bac™ baculovirus expression systems manual.

a) Transposition of DH10Bac E coli Cells

One ng (5 μl) of the recombinant pFastBac-1 construct containing the nucleotide sequence encoding the porcine $\alpha_2\delta$-1 deletion mutant of SEQ ID NO:9 was added to 100 µl of DH10Bac cells thawed on ice. The cells were then mixed gently by tapping the tube then incubated on ice for 30 minutes before heat shock treatment by incubation in a 42° C. water bath for 45 seconds. The mixture was then chilled on ice for 2 minutes before the addition of 900 µl of S.O.C. medium. The mixture was then placed in a shaking incubator (200 rpm) at 37° C. for 4 hours. The cells were then serially diluted (10 fold dilutions from $10^{-1}$ to $10^{-3}$) and 10 µl of each dilution plated on LB agar plates containing 50 µg/ml gentamicin, 10 µg/ml tetracycline, 100 µl/ml Bluo-gal and 40 µg/ml IPTG. The plates were incubated at 37° C. for between 1 and 3 days until discrete colonies of blue and white colour were discernible.

b) Isolation of Recombinant DNA

White colonies (containing the recombinant bacmid) were picked and grown for 24 hours (to stationary phase) at 37° C. with shaking (200 rpm) in 2 ml of LB containing 50 µg/ml kanamycin, 7 µg/ml gentamicin and 10 µg/ml tetracycline. 1.5 ml of culture was then transferred to a microfuge tube and centrifuged at 14,000×g for 1 minute. The supernatant was removed and the cells resuspended gently in 0.3 ml of 15 mM Tris-HCl (pH8.0), 10 mM EDTA, 100 µg/ml RNase A. 0.3 ml of 0.2 N NaOH, 1% SDS was then added and the mixture mixed gently before incubation at 22° C. for 5 minutes. Then 0.3 ml of 3 M potassium acetate (pH5.5) was added and the sample placed on ice for 10 minutes. After centrifugation at 14,000×g for 10 minutes the supernatant was transferred to a tube containing 0.8 ml of isopropanol, mixed then placed on ice for 10 minutes before centrifugation at 14,000×g for 10 minutes. The supernatant was then discarded and the pellet rinsed with 0.5ml of 70% ethanol before centrifugation at 14,000×g for 5 minutes. This 70% ethanol rinse was then repeated before removing all of the supernatant and air drying the pellet for 10 minutes at room temperature. The pellet was finally resuspended in 40 µl of TE.

c) Transfection of sf9 Cells with the Recombinant Bacmid DNA

A 6-well tissue culture plate was seeded with 0.9×10⁶ sf9 cells (cells at log phase having grown from a culture passaged at 0.3×10⁶ cells/ml) per 35 mm well in 2 ml of Sf-900 II SFM media containing 50 units/ml penicillin and 50 g/ml streptomycin. Cells were left to attach at 27° C. for 1 hour. Bacmid DNA prepared as described above (5 µl) was added to 200 µl of Sf-900 II SFM media containing 6 µl of CELLFECTIN and mixed before incubation at room temperature for 45 minutes. The cells were washed once with 2 ml of Sf-900 II SFM media without antibiotics then 0.8 ml of Sf-900 II SFM media was added to each tube containing the lipid-DNA complex. The wash buffer was removed from the cells and the 1 ml of diluted lipid-DNA complex overlaid on the cells. The cells were incubated for 5 hours at 27° C. after which time the transfection mixture was removed and 2 ml of Sf-900 II SFM media containing 50 units/ml penicillin and 50 µg/ml streptomycin was added. The cells were then incubated for 72 hours.

After incubation for 72 hours the media was removed from the cells and centrifuged at 500×g for 5 minutes. The supernatant was then transferred to a fresh tube, this was labelled as the P0 bank and stored at 4° C. in the dark. The P1 bank was prepared by passaging sf9 cells at approx 5×10⁶ cells/ml to 2×10⁶ cells/ml (100 ml in a 250 ml Erlenmeyer flask) and adding 0.5 ml of the P0 bank harvested above. The cells were then incubated shaking (200 rpm) at 27° C. for 4 days. Under sterile conditions the culture was centrifuged at 500×g for 10 minutes and the supernatant 0.2 µM filtered (P1 bank). The P2 bank was prepared by adding 2 ml of P1 bank per 400 ml culture (in 1 L Erlenmeyer flasks) passaged as above to 2×10⁶cells/ml. The culture was incubated as before for 4 days and the supernatant harvested and filtered as described for the P1 bank. The supernatant was first pooled then aliquoted (10 ml) and stored at 4° C.

EXAMPLE 4

Protein Expression

To sf9 cells passaged from ~5×10⁶ cells/ml to 2×10⁶ cells/ml in Sf-900 II SFM media was added 0.1 ml virus per 100 ml of cells of the appropriate viral bank (400 ml volumes in 1 L Erlenmeyer flasks). The cells were then cultured for 4–5 days at 27° C. with 110 rpm shaking. Expression of the protein was confirmed by SDS-PAGE and Western blotting using an anti penta-His monoclonal antibody (Qiagen) and was detected in the culture supernatant and cell lysate.

EXAMPLE 5

Purification of $\alpha_2\delta$-1 Deletion Mutant of SEQ ID NO: 9

The $\alpha_2\delta$-1 deletion mutant of SEQ ID NO: 9 was purified from the cell lysate following the purification strategy outlined below:

The culture was centrifuged at 6,000×g for 10 minutes and the supernatant removed. The weight of the cell pellet was determined before re-suspension in 20 mM Tris pH 8.0, 100 mMKCl, 1% P40-Nonidet (100 ml per 20 g of wet cells). A protease inhibitor cocktail (Sigma Cat# P8849), 1 ml/L, was added to the mixture. The solution was then stirred for 10 minutes before centrifugation for 1 hour at 30,000×g and 4° C. The supernatant was concentrated (30 kDa cut off) to approx.~300 ml then centrifuged for 1 hour at 100,000×g.

Supernatant containing the soluble proteins was diluted 1:3 in 10 mM Tris-HCl pH 8.0 (equilibration buffer) and loaded onto a pre-equilibrated Q-Sepharose column (2.5 cm i.d.×30 cm h.) at a flow rate of 900 ml/h. After washing with equilibration buffer until a stable $A_{280nm}$ baseline had been achieved, protein was eluted with 20 mM Tris-HCl pH 8.0, 0.5 M KCl, 10 mM Imidazole.

The eluate was then loaded onto a Ni-NTA (Qiagen) column (2.5 cm i.d.×6 cm h.) pre-equilibrated in 20 mM Tris pH8.0, 0.5M KCl, 10 mM Imidazole at a flow rate of 2 mg/min. The column was washed successively with buffer A (20 mM Tris pH8.0, 0.5M KCl, 20 mM Imidazole), buffer B (100 mM Tris-HCl pH8.0, 1M KCl), and buffer A again. Elution was performed with buffer C (20 mM Tris-HCl pH8.0 100 mM KCl, 0.5M Imidazole). The Ni-NTA eluate (~50 ml) was concentrated (30 kDa cut-off) to ~2 ml and applied at 1 ml/min and in 0.2 ml aliquots, to an FPLC Superdex-200 column equilibrated in 10 mM HEPES, pH7.4, 150 mM NaCl. Fractions containing the polypeptide of SEQ ID NO:9 were pooled. As shown in FIG. 1, the protein elution profile and associated [³H]gabapentin binding activity is presented together with a silver-stained SDS-PAGE gel (post Ni NTA load of Superdex-200) demonstrating the co-elution of the ~130 kDa band ($\alpha_2\delta$) with the [³H]gabapentin binding activity and $A_{280nm}$ profile.

EXAMPLE 6

SPA Assay of [³H]Gabapentin Binding to Soluble Porcine $\alpha_2\delta$-1b-6His

The assay was carried out at 20° C. Assay components were added in the following order (all reagents were diluted in 10 mM HEPES (pH 7.4 at 21° C.) to 96-well Optiplates:

| 25 μl | imidazole at various concentrations (diluted from a 1M stock pH 8.0, see assay details) |
|---|---|
| 50 μl | 10 mM HEPES pH 7.4 |
| 25 μl | (50 mg) SPA beads (Amersham) |
| 100 μl | s-α$_2$δ-1b-6His of SEQ ID NO:9 (2 μl protein diluted to 100 μl) obtained from example 5 |
| 25 μl | radioligand ([$^3$H]gabapentin) |

Immediately after adding radioligand, the optiplates were loaded in the Packard Top Count scintillation counter to follow the binding time course. Imidazole was first used in the assay to optimize the specific interaction of the protein's 6His tag with the SPA bead. Imidazole itself (up to 100 mM) in the filtration assay has no effect on [$^3$H]gabapentin binding (n=1).

Figure 2:
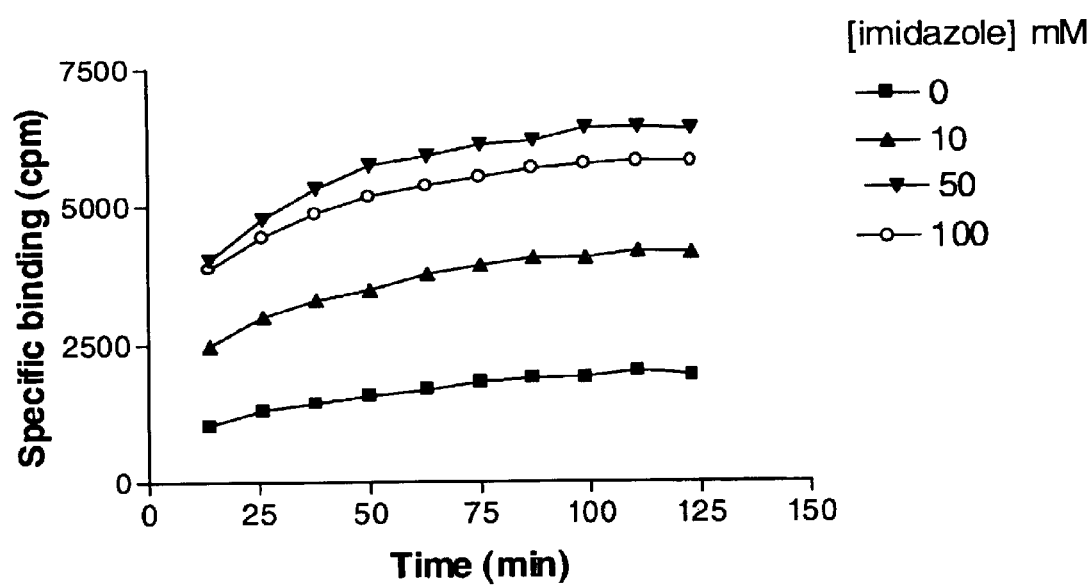
FIG. 2 illustrates the optimization of imidazole concentrations in an embodiment of the SPA assay of the invention.

As shown in FIG. 2, specific binding of [$^3$H]gabapentin to the s-α$_2$δ-1b-6His was enhanced by imidazole. Of the concentrations, tested the optimal was 50 mM. Equilibration was reached after ~2 hours.

EXAMPLE 7

Ni Flashplate assay of [$^3$H]gabapentin binding to soluble porcine α$^2$δ-1b-6His (SEQ ID NO:9)

Assays were carried out at 21° C. in a final volume of 250 μl in 96-well NEN Ni chelate flash plates. Assay components were added in the following order (all reagents were diluted in 10 mM HEPES (pH 7.4 at 21° C.)):

| 25 μl | 10 mM HEPES pH 7.4 |
|---|---|
| 25 μl | imidazole at various concentrations (diluted from a 1M stock pH 8.0, see assay details) |
| 75 μl | 10 mM HEPES pH 7.4 |
| 100 μl | s-α$_2$δ-1b-6His (2 μl protein diluted to 100 μl) obtained from example 5 |
| 25 μl | radioligand ([$^3$H]gabapentin) |

Immediately after adding the radioligand, flash plates were loaded in the Packard Top Count scintillation counter to follow the binding time course. The '[$^3$H] flash plate' programme (cpm) was used to monitor activity. Imidazole was first used in the assay to optimize the specific interaction of the protein's 6His tag with the Ni flashplate. Imidazole itself (up to 100 mM) in the filtration assay has no effect on [$^3$H]gabapentin binding (n=1).

Figure 3:
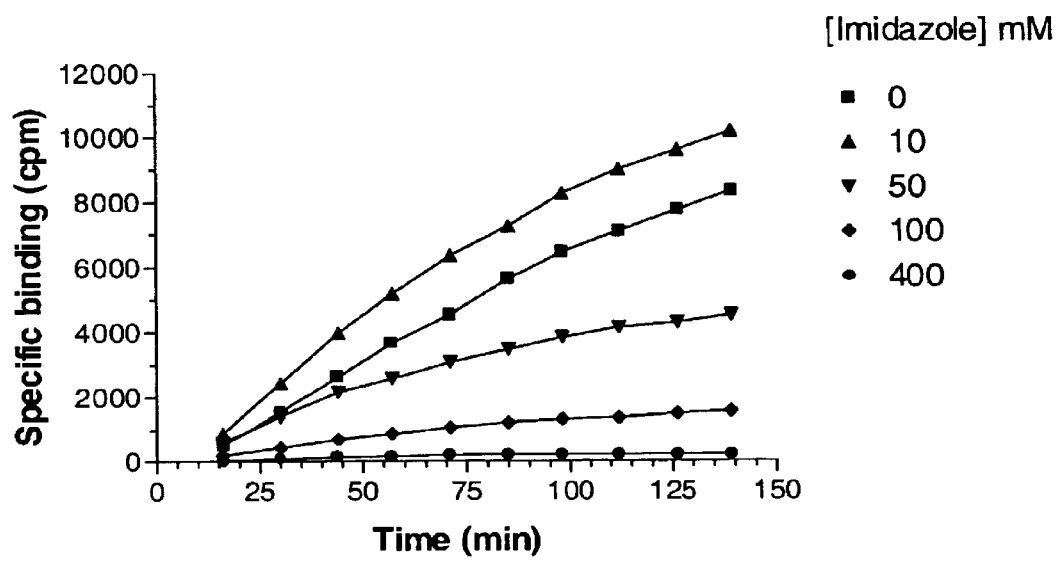
FIG. 3 illustrates the optimization of imidazole concentrations in an embodiment of the flashplate assay of the invention.

As shown in FIG. 3, the specific binding of [$^3$H]gabapentin to the s-α$_2$δ-1b-6His was enhanced by imidazole. Initially, from the concentrations tested, the best concentration was found to be 10 mM.

Figure 4:
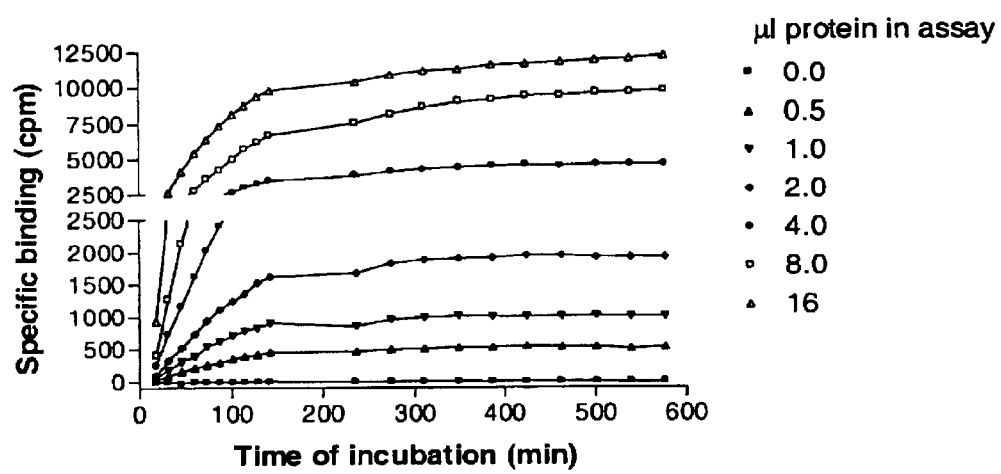
FIG. 4 illustrates the flashplate time course of [³H] gabapentin binding to various concentrations of the recombinant polypeptide with the amino acid sequence of SEQ ID NO:9.
Figure 5:
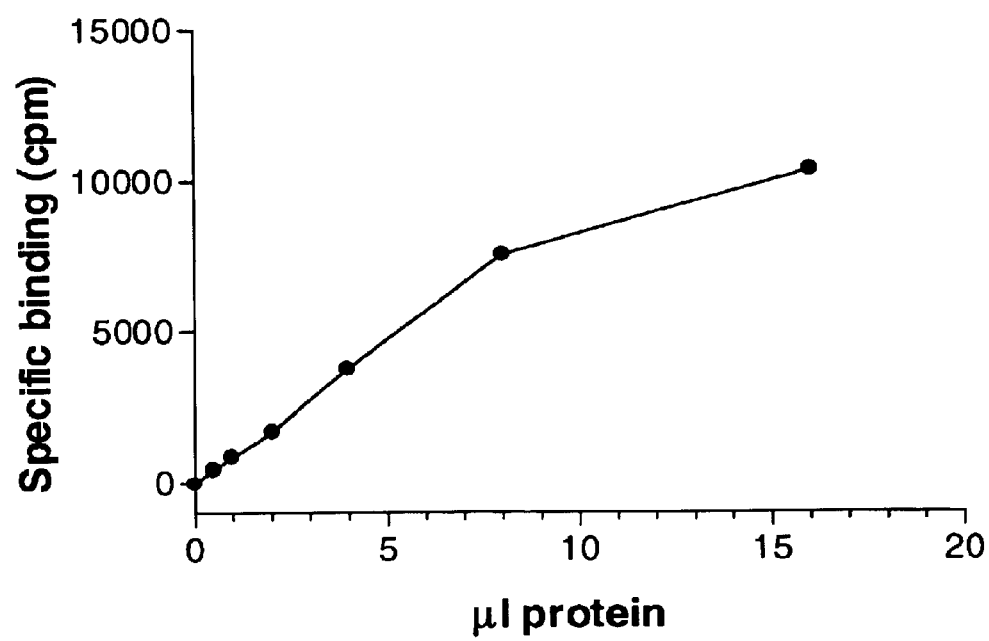
FIG. 5 illustrates the capacity of the recombinant polypeptide with the amino acid sequence of SEQ ID NO:9 in a flashplate assay after 3 hours of incubation.
Figure 6:
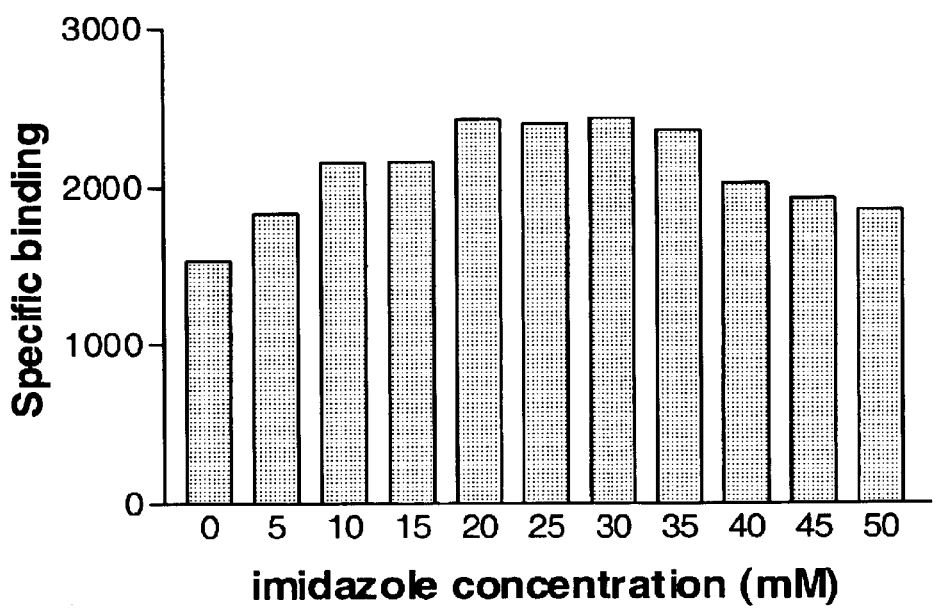
FIG. 6 illustrates the optimum imidazole concentration, assayed after 3 hours of incubation, required to maximize [³H]gabapentin binding using a constant amount of the recombinant polypeptide with the amino acid sequence of SEQ ID NO:9.
Figure 7:
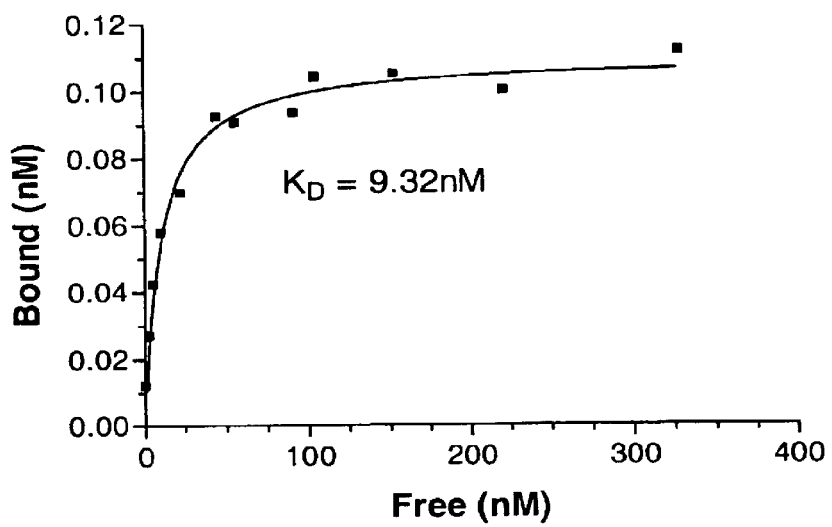
FIG. 7 illustrates flashplate assay of [³H]gabapentin saturation binding to the purified recombinant polypeptide with the amino acid sequence of SEQ ID NO:9, assayed after 3 hours of incubation.
Figure 7:
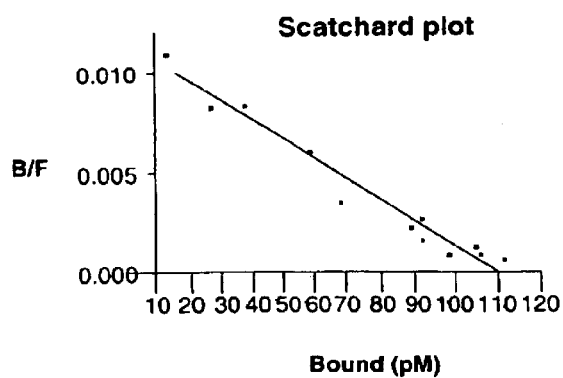

Specific binding was determined at different volumes of s-α$_2$δ-1b-6His, in the presence of 10 mM imidazole, over a time period of 10 h. Results are shown in FIG. 4 and equilibrium was reached at ~3 h. Specific binding increased linearly with increasing amounts of protein, up to 8 μl, after which the binding capacity of the Ni chelate in the assay well was probably exceeded (see FIG. 5). The published maximum binding capacity of NEN plates is 6 pmol/well. The concentration of purified s-α$_2$δ-1b-6His is estimated at ~0.6 pmol/μl, which yields 5 pmol/well at 8 μl.

TABLE 2

Saturation studies
Saturation experiments were performed with 12 duplicate data points, [$^3$H]gabapentin concentration ranged from ~1 to 350 nM. Data was analyzed using KEL-RADLIG for Windows.

| Flash plate (2 μl protein used, n = 2) | Filter binding K$_D$(nm) (4 μl protein used, n = 3) |
|---|---|
| K$_D$, 9.32 nM | K$_D$, 12.3 nM |
| K$_D$, 10.5 nM | K$_D$, 8.91 nM |
| | K$_D$, 10.6 nM |
| Mean = 9.91 nM | Mean = 10.60 ± 0.98 nM |

EXAMPLE 8

Ni Flashplate Assay of [$^3$H]Leucine Binding to Soluble Porcine α$_2$δ-1b-6His

Figure 8:
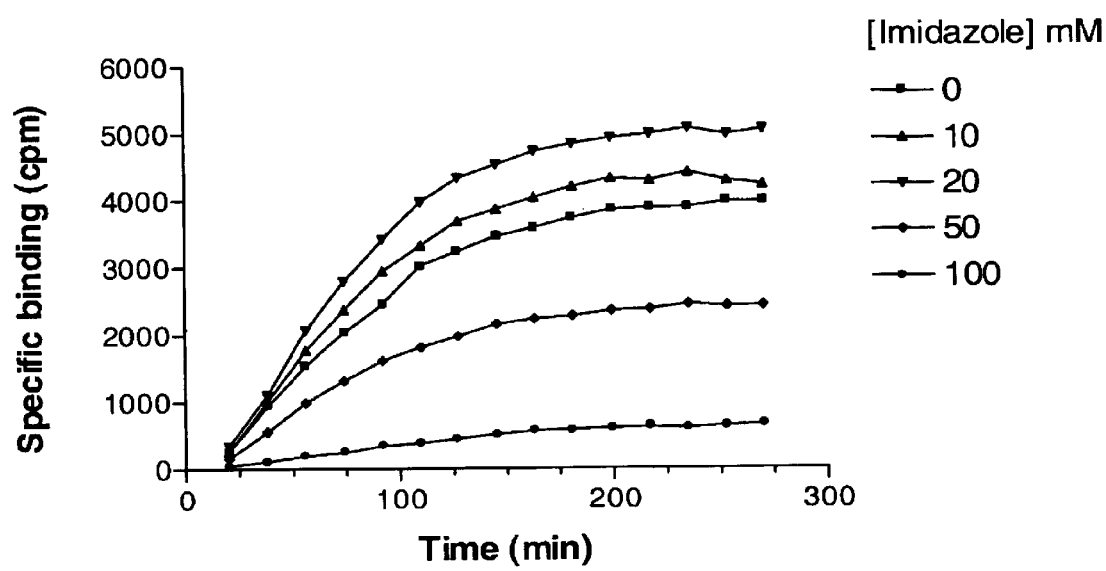
FIG. 8 illustrates the flashplate time course optimization of imidazole concentration required to maximize the [³H] Leucine binding window to the purified recombinant polypeptide with the amino acid sequence of SEQ ID NO:9, assayed after 3 hours of incubation.

The procedure described in example 2 was repeated, except that [$^3$H]gabapentin was replaced by 25 μl (10.1 nM) of [$^3$H]Leucine, as shown in FIG. 8, [$^3$H]Leucine binds with high affinity to soluble α$_2$δ-1b-6His. This demonstrates that it is possible to use commercially available forms of [3H] Leucine in replacement of [$^3$H]gabapentin in the assay.

EXAMPLE 9

Ni Flashplate assay studying competitive binding of [$^3$H]gabapentin, (S+)-3-isobutyl GABA and (R−)-3-isobutyl GABA to porcine α$_2$δ-1b-6His (SEQ ID NO:9)

Assays were carried out at 21° C. in a final volume of 250 μl in 96-well NEN Ni chelate flash plates. Wells were set up for both 'total' and 'non-specific' binding. Specific binding was defined as that remaining after subtraction of the average of the 'non-specific binding' values from the average of the 'total' following order (all reagents were diluted in 10 mM HEPES (pH 7.4 at 21° C.)):

| | 25 μl | 10 mM HEPES pH 7.4 or 25 μl of the test compound at the appropriate concentration in HEPES |
|---|---|---|
| | 25 μl | 200 mM imidazole (diluted from a 1M stock pH 8.0, see assay details) |
| Total binding | 75 μl | 10 mM HEPES pH 7.4 |
| Non-specific binding | 50 μl | 10 mM HEPES pH 7.4 and 25 μl 100 μM (S+)-3-isobutyl GABA |
| | 100 μl | s-α$_2$δ-1b-6His (2 μl protein* diluted to 100 μl) |
| | 25 μl | radioligand ([$^3$H]gabapentin or [$^3$H]Leucine) |

*The source of s-α$_2$δ-1b-6His was that purified by FPLC Superdex-200 gel filtration (see example 5)

Immediately after adding radioligand, flash plates were loaded in the Packard Top Count scintillation counter to follow the binding time course. Incubation time before the assay was 3 hours. The '[$^3$H] flash plate' programme (cpm) was used to monitor activity. Specific binding was ~98% of the 'total' value. Imidazole was used in the assay to optimize the specific interaction of the protein's 6His tag with the Ni flashplate. Imidazole itself (up to 100 mM) in the filtration assay has no effect on [$^3$H]gabapentin binding (n=1).

Competition studies were compared across the flash-plate and filter binding methodologies in order to validate the new assay technology with the established filter binding methodology.

Figure 9:
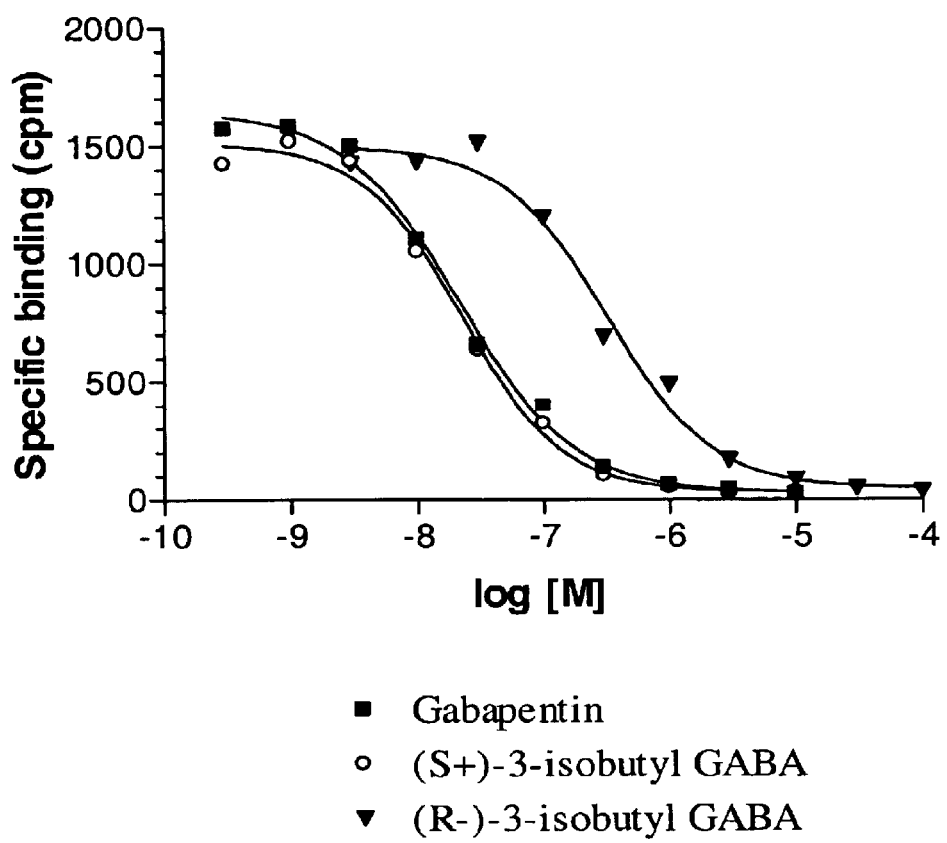
FIG. 9 illustrates competition curves of three compounds in the flashplate assay format, assayed after 3 hours of incubation.

GraphPad Prism software was used to process competition curve data and determine $IC_{50}$ and hill slope values. Twelve point competition curves with half log dilution steps of test compounds were used in the experiments. Results are shown in Table 3 below where IC50 values are presented, and in FIG. 9 where hill slopes range from −0.9 to 1.3. The [$^3$H]Gabapentin concentration used in assay is in the range of 10–13 nM

TABLE 3

| Test compound | Flash plate (3 µl protein used, n = 2) | Filter binding $K_D$(nm) (4 µl protein used, n = 3) |
|---|---|---|
| Gabapentin | 10.4 | 7.13 |
|  | 7.97 | 7.70 |
|  |  | 10.2 |
| Mean (geometric) | 9.10 nM | 7.84 nM |
| (S+)-3-isobutyl GABA | 10.9 | 6.52 |
|  | 7.58 | 6.21 |
|  |  | 8.29 |
| Mean (geometric) | 9.09 nM | 6.95 nM |
| (R-)-3-isobtyl GABA | 157 | 78.4 |
|  | 207 | 64.2 |
|  |  | 107 |
| Mean (geometric) | 180 nM | 81.5 nM |

Competition studies:
GraphPad Prism software was used to process competition curve data and determine $IC_{50}$ and hill slope values. Ten point competition curves with half log dilution steps of test compounds were used in the experiments.
$IC_{50}$ values were converted to Ki values (presented in table) according to the following equation: Ki = $IC_{50}/(1 + [L]/K_D)$
The $K_D$ values used were those mean values presented in table 1.
The [$^3$H]Gabapentin concentration in the assay ranged from 10–13 nM and was determined for each experiment for the purpose of calculating the Ki value as described above. Hill slopes were all in the range of −0.9 to 1.3

EXAMPLE 10

Filter binding assay of [$^3$H]gabapentin binding to the recombinant polypeptide of SEQ ID NO:9

Assays were carried out at 21° C. in a final volume of 250 µl in 96-deep well plates. Assay components were (all reagents were diluted in 10 mM HEPES (pH 7.4 at 21° C.)):

| | |
|---|---|
| 25 µl | compound to test |
| 200 µl | Polypeptide of SEQ ID NO:9 (3 µl protein diluted to 200 µl) |
| 25 µl | radioligand ([$^3$H]gabapentin (65Ci/mmole) |

Plates were incubated at room temperature for 1 h prior to filtering on to 96-well GF/B Unifilter plates pre-soaked in 0.3% polyethylenimine. Filters were washed with 3×1 ml 50 mM Tris-HCl (pH 7.4 at 4° C.), and dried over-night. Scintillant (Microscint O, 50 µl) was added and the plates counted using a Packard Top Count scintillation counter. Specific binding was ~98% of the 'total' value. In [$^3$H] gabapentin saturation studies, the $K_D$ (nM) obtained was about 10.62.

REFERENCES

Perez-Reyes, E., and Schneider, T. (1994) *Drug Dev. Res.* 33, 295–318
Catterall, W. A. (1995) *Annu. Rev. Biochem.* 64, 493–531
Bimbaumer, L., Campbell, K. P., Catterall, W. A., Harpold, M. M., Hofmann, F., Home, W. A., Mori, Y., Schwartz, A., Snutch, T. P., Tanabe, T., and Tsien, R. W. (1994) *Neuron* 13, 505–506
Brust, P. F., Simerson, S., McCue, A. F., Deal, C. R., Schoonmaker, S., Williams, M. E., Velicelebi, G., Johnson, E. C., Harpold, M. M., and Ellis, S. B. (1993) *Neuropharmacology* 32,1089–1102
Itagaki, K., Koch, W. J., Bodi, L, Klockner, U., Slish, D. F., and Schwartz, A. (1992) *FEBS Lett.* 297, 221–225
Mikami, A., Imoto, F_Tanabe, T., Nidome, T., Mori, Y., Takeshima, H., Narumiya, S., and Numa, S. (1989) *Nature* 340, 230–233
Mori, Y., Friedrich, T., Kim, M. S., Mikami, A., Nakai, J., Ruth, P., Bosse, E., Hofmann, F., Flockerzi, V., Furuichi, T., Mikoshiba, K., Imoto, K, Tanabe, T., and Numa, S. (1991) *Nature* 350,398–402
Singer, D., Biel, M., Lotan, I., Flockerzi, V., Hofmann, F., and Dascal, N. (1991) *Science* 253,1553–1657
Ramsay, R. E. (1994) *Neurology* 44, Suppl. 5, 23–30
Watson, W. P., and Little, H. J. (1995) *Br. J. Pharmacol.* 116, 33P(abstr.)
Singh, L., Field, M. J., Ferris, P., Hunter, J. C., Oles, R. J., Williams, R. G., and Woodruff, G. N. (1996) *Psychopharmacology* 127, 1–9
Xiao, W. H., and Bennet, G. L (1995) *Soc. Neurosci.* 21, 897 (abstr.)
Mellick, G. A., Mellicy, L. B., and Mellick, L. B. (1995) *J. Pain Symptom Manage.* 10, 265–266
Shimoyama, N., Shimoyama, M., Davis, A. M., Inturrisi, C. E., and Elliott, K. J. (1997) *Neurosci. Lett.* 222, 65–67
SegaL A. Z., and Rordorf, G. (1996) *Neurology* 46, 1175–1176
Mellick, G. A., and Mellick, L. B. (1996) *Sleep* 19, 224–226
Patel, J., and Naritoku, D. K (1996) *Clin. Neuropharmacol.* 19,185–188
Suman Chauhan, N., Webdale, L., Hill, D. R., and Woodruff, G. N. (1993) *Eur, J. Pharmacol.* 244, 293–301
Macdonald, R. L., and Kelly, F_M. (1993) *Epilepsia* 34, Suppl. 5, S1–S8
Taylor, C. P. (1994) *Neurology* 44, Suppl. 5, 10 −16
Gotz, E., Feuerstein, T. J., Lais, A., and Meyer, D. K (1993) *Arzneimittelforschung* 43, 636–638
Loscher, W., Honack, D., and Taylor, C. P. (1991) *Neurosci. Lett.* 128,150–154
Honmou, O., Knesis, J. D., and Richerson, G. B. (1995) *Epilepsy Res.* 20, 193–202

Honmou, O., Oyelese, A. A., and Kocsis, J. D. (1995) *Brain Res.* 692,273–277

Petroff, O. A. C., Rothman, D. L., Behar, K. L., Lamoureux, D., and Mattson, R. H. (1996) *Ann. Neurol.* 39, 95–99

Reimann, W. (1983) *Eur. J. Pharmacol* 94, 341–344

Dooley, D. J., Bartoszyk, G. D., Hartenstein, J., Reimann, W., Rock, D. M., and Satzinger, G. (1986) *Golden Jubilee Conference and Northern European Epilepsy Meeting*. Abstracts, University of York, UK, September 1986 (Abstract 8).

Thurlow, R. J., Brown, J. P., Gee, N. S., Hill, D. R., and Woodruff, G. N. (1993) *Eur. J. Pharmacol.* 247,341–345

Gee, N. S., Brown, J. P., Dissanayake, V. U. I,, Offord, J., Thurlow, R., and Woodruff, G. N. (1996) *J. Biol. Chem.* 271, 5768–5776

Dissanayake, V. U. I-, Gee, N. S., Brown, J. P., and Woodruff, G. N. (1997) *Br. J. Pharmacol.* 120, 833–840

Taylor, C. P., Vartanian, M. G., Yuen, P. W., Bigge, C., Suman Chauhan, N., and Hill, D. R. (1993) *Epilepsy Res.* 14,11–15

Rock, D. M., Kelly, K. M., and Macdonald, R. L. (1993) *Epilepsy Res.* 16, 89 –98

Wamil, A. W., Mclean, M. J., Nashville, T. N., and Taylor, C. P. (1991) *Neurology* 41, Suppl. 1, 140 (abstr.)

De Jongh, K S., Warner, C., and Catterall, W. A. (1990) *J. Biol. Chem.* 265, 14738–14741

Jay, S . D., Sharp, A. H., Kahl, S. D., Vedvick, T. S., Harpold, M. M., and Campbell, K. P. (1991) *J. Biol. Chem.* 266, 3287–3293

Burgess, A. J., and Norman, R. 1. (1988) *Eur. J. Biochem.* 178, 527–533

Ellis, S. B., Williams, M. E., Ways, N. R., Brenner, R., Sharp, A. H., Leung, A. T., Campbell, K. P., McKenna, E., Koch, W. J., Hai, A., Schwartz, A., and Harpold, M. M. (1988) *Science* 241, 1661–1664

Brickley, K., Campbell, V., Berrow, N., Leach, R., Norman, R. I., Wray, D., Dolphin, A. C., and Baldwin, S. A- (1995) *FEBS Lett.* 364,129–133

Brice, N. L., Berrow, N. S., Campbell, V., Page, K. M., Brickley, K., Tedder, I., Dolphin, A C. (1997) *Eur. J. Neurosci.* 9, 749–759

Wiser, O., Trus, M., Tobi, D., Halevi, S., Giladi, E., and Atlas, D. (1996) *FEBS Lett.* 379,15–20

Xu, X., and Arnason, U. (1994) *Gene (Amst.)* 148, 357–362

Williams, M. E., Feldman, D. H., McCue, A. F., Brenner, R., Velicelebi, G., Ellis, S. B., and Harpold, M. M. (1992) *Neuron* 8, 71–84

Kim, H. L., Kim, H., Lee, P., King, R. G., and Chin, H. (1992) *Proc. Natl. Acad Sci. U.S.A.* 89,3251–3255

Brown, J. P., Dissanayake, V. U. K., Briggs, A. R., Milic, M. R., and Gee, N. S. (1998) *Anal. Biochem.* 255, 236–243

Higuchi, R. (1990) in PCR Protocols: *A Guide to Methods and Applications* (Innis, M. A., Gelfand, D. H., Sninsky, J. J., and White, T.J. eds) pp. 177–187, Academic Press, Ltd., London Bradford, M. M. (1976) *Anal. Biochem.* 72, 248–252

Kyte, J., and Doolittle, F. (1982) *J. Mol. Biol.* 157, 105–132

Summers, M. F., Henderson, L. E., Chance, M. R., Bess, J. W., Jr., South, T. L., Blake, P. R., Sagi, I., Perez-Alvarado, G., Sowder, R. C., Hare, D. R., and Arthur, L. O. (1992) *Protein Sci.* 1, 563–574

Klug, A. and Rhodes, D. (1987) *Trends. Biochem. Sci.* 12, 464–469

Pieler, T., and Bellefroid, E. (1994) *Mol. Biol. Rep.* 20, 1–8

Preston, R. A., Manolson, M. F., Becherer, M, Weidenhammer, E., Kirkpatrick, D., Wright, R., and Jones, E. W. (1991) *Mol. Cell, Biol.* 11, 5801–5812

Tan, X., Waterham, H. R., Veenhuis, M., and Cregg, J. M. (1995) *J. Cell Biol.* 128,307–319

Scotland, P. B., Colledge, M., Melnikova, I., Dai, Z., and Froehner, S. C. (1993) *J. Cell Biol.* 123, 719–728

Henderson, L. E., Copeland, T. D., Sowder, R. C., Smythers, G. W., and Oroszlan, S. (1981) *J. Biol. Chem.* 256, 8400–8406

Beaucage et al., *Tetrahedron Lett* (1981) 22: 1859–1862.

Brown El., Belagaje R, Ryan M J, Khorana H G, *Methods Enzymol* (1979); 68, 109–151.

Feldman and Steg, (1996) *Medecine/Sciences, synthese,* 12, 47–55.

Houbenweyl, (1974), in *Meuthode der Organischen Chemie*, E. Wunsch Ed., Volume 15-I et 15-II, Thieme, Stuttgart.

Koch Y. (1977), *Biochem. Biophys. Res. Commun.*, 74, 488–491.

Kohler G. and Milstein C., (1975) *Nature*, 256, 495.

Kozbor et al., (1983) *Hybridoma*, 2(1), 7–16.

Leger O J, et al. (1997) *Hum Antibodies*, 8(1), 3–16.

Martineau P, Jones P, Winter G. (1998), *J. Mol Biol*, 280(1), 117–127.

Merrifield R B, 1965*a*, *Nature*, 207(996), 522–523.

Merrifield R B, 1965*b*, *Nature*, 207 (996), 22–523.

Narang S A, Hsiung H M, Brousseau R, *Methods Enzymol* 1979, 68, 90–98.

Ohno et al., (1994), *Science*, 265, 781–784.

O' Reilly et al., (1992) Baculovirus expression vectors: a Laboratory Manual. W.H. Freeman and Co., N.Y.

Ridder R. Schmitz R, Legay F, Gram H. (1995) *Biotechnology* (NY), 13(3), 255–260.

Smith et al., (1983), *Mol. Cell. Biol.*, 3, 2156–2165.

Sternberg N. L. (1992), *Trends Genet*, 8, 1–16.

Sternberg N. L. (1994) *Mamm. Genome*, 5, 397–404.

Sambrook, J. Fritsch, E. F. and T. Maniatis (1989). Molecular cloning: a laboratory manual, 2ed. Cold Spring Harbor Laboratory, Cold Spring Harbor, N.Y.

Sanchez-Pescador R., (1988), *J. Clin. Microbiol.*, 26(10), 1934 –1938.

Urdea et al., M S (1988) *Nucleic Acids Research*, 11, 4937–4957.

Urdea et al., M S (1991) *Nucleic Acids Symp Ser.*, 24, 197–200.

What is claimed is:

1. A method for the screening of ligands which bind a cerebral cortical voltage-dependent calcium channel $\alpha_2\delta$-1 subunit, said method comprising the steps of:

contacting a secreted soluble recombinant calcium channel $\alpha_2\delta$-1 subunit polypeptide selected from the group consisting of SEQ ID NO: 13, 14 and 15 with:

a ligand of interest;

a labelled compound which binds the $\alpha_2\delta$-1 subunit; and measuring the level of binding of the labelled compound to the $\alpha_2\delta$-1 subunit.

2. A method according to claim 1, wherein said contacting and said binding is in a well of a flashplate.

3. A method according to claim 1, wherein said secreted soluble recombinant calcium channel $\alpha_2\delta$-1 subunit polypeptide is SEQ ID NO: 15.

* * * * *

SEQUENCE LISTING

<160> NUMBER OF SEQ ID NOS: 21

<210> SEQ ID NO 1
<211> LENGTH: 3842
<212> TYPE: DNA
<213> ORGANISM: Sus scrofa

-continued

<400> SEQUENCE: 1

```
gggggattgat cttcgatcgc gaagatggct gctggctgcc tgctggcctt gactctgaca        60
cttttccaat ctttgctgat cggtccctca tcgcaggagc cgttcccgtc ggccgtcact       120
atcaagtcat gggtggataa aatgcaagaa gaccttgtca ccctggcaaa aacagcaagt       180
ggagtcaatc agcttgtcga tatttatgaa aaataccaag attttgtatac tgtgaaccca      240
aataatgcac gccagctggt ggaaattgca gccagggata ttgagaaact tctgagcaac       300
agatctaaag ccctggtgcg cctagctttg gaagcagaga aggttcaagc agcccaccag       360
tggagagagg attttgcaag caatgaagtt gtctactaca atgcaaagga tgatctcgat       420
cctgaaaaaa atgacagtga gccaggcagc cagaggataa aacctgtttt tattgatgat       480
gctaattttg ggcgacagat atcttatcag catgcagcag tccatattcc caccgacatc       540
tatgagggct caacaattgt gttaaatgaa ctgaactgga caagtgcctt agatgaagtt       600
ttcaagaaaa atcgagagga agatccctca ttattgtggc aggtgtttgg cagtgccaca       660
ggcctggccc ggtattatcc agcttctcca tgggttgata acagtagaac tccaaacaag       720
attgaccttt atgatgtacg aaggagacca tggtacatcc aaggagctgc atctcctaaa       780
gatatgctta ttctggtcga cgtgagtgga agtgttagtg gtttgacgct taaactgatc       840
cgaacatctg tctctgaaat gttggaaacc ctctcagatg acgattttgt gaatgtagct       900
tcatttaaca gcaatgccca ggatgtaagc tgttttcaac accttgtcca agcaaatgta       960
agaaataaga aagtgctgaa agatgcagtt aataatatca cagcaaaagg aatcacagat      1020
tacaagaagg gctttagttt tgcttttgaa caactgctta attataacgt ttctagagcc      1080
aactgcaata agattatcat gttgttcacc gatggaggag aagagagagc tcaggagata      1140
tttgccaaat acaacaaaga caaaaaagta cgtgtattca catttttcagt tggtcaacat      1200
aattatgaca gaggacctat tcagtggatg gcctgtgaaa ataaaggtta ttattatgaa      1260
attccttcca ttggagcaat cagaatcaat actcaggaat attttggatgt tctgggaaga      1320
ccaatggttt tagcaggaga caaagctaag caagtccagt ggacaaacgt gtacctggat      1380
gcactggaac tgggacttgt cattactgga actcttccgg tcttcaacat aaccggccaa      1440
aatgaaaata gacgaacttt aaagaaccag ctgattcttg gtgtgatggg agttgatgta      1500
tctttggaag atattaaaag actgacacca cgttttacac tgtgcccaa tggctattac       1560
tttgcaattg atcctaatgg ctatgtttta ttacatccaa atcttcagcc aaagaacccc      1620
aaatctcagg agccagtaac cttggatttc cttgatgcag aattagagaa tgatattaaa      1680
gtggagatcc gaaataaaat gatagatgga gaaagtggag aaaaaacatt cagaactctg      1740
gttaaatctc aagatgagag atatattgac aaaggaaaca ggacatatac atggactcct      1800
gtcaatggca cagattacag tttggccttg gtattaccaa cctacagttt ttactatata      1860
aaagccaaaa tagaagagac aataactcag gccagatcaa aaaagggcaa aatgaaggat      1920
tcagaaacac tgaagcctga taatttttgaa gaatctggct atacattcat agcaccaaga      1980
gactactgca atgaccttaa aatatcagat aataataccg aatttctttt aaactttaat      2040
gagtttattg ataaaaaac tccaaacaac ccgtcatgca acacagattt gattaataga      2100
gtcttgctgg atgcgggctt tacaaatgaa cttgtccaaa attactggag taagcagaaa      2160
aacatcaagg gagtgaaagc acggtttgtt gtaactgatg gagggattac cagagtttat      2220
cccaaagagg ctggagaaaa ttggcaagaa aacccagaaa catatgagga cagcttctat      2280
```

| | |
|---|---:|
| aaaagaagtc tagataacga taactatgtt ttcactgctc cctactttaa caaaagtgga | 2340 |
| cctggtgctt atgaatcagg catcatggta agcaaagctg tagaaatata catccaagga | 2400 |
| aaacttctta aacctgcagt tgttggaatt aaaattgatg taaattcctg datagagaat | 2460 |
| ttcaccaaaa catcaatcag ggatccgtgt gctggtccag tttgtgattg taaaagaaac | 2520 |
| agtgatgtaa tggattgtgt gattctagat gatggtgggt ttcttttgat ggcaaatcat | 2580 |
| gatgattata ctaaccagat tggaaggttt tttggagaga ttgacccaag tttgatgaga | 2640 |
| cacctggtta atatatcagt ttatgctttt aacaaatctt acgattatca gtcagtgtgt | 2700 |
| gagcctggtg ctgcaccaaa acaaggagca ggacatcgct cagcatatgt gccatcaata | 2760 |
| gcagacatct tacacattgg ctggtgggcc actgcagctg catggtctat tctacagcag | 2820 |
| tttctcttga gtttgacctt tccacgactt cttgaagcag ttgagatgga agatgatgac | 2880 |
| tttaccgcct ctctgtcaaa gcagagttgc attactgaac aaacccagta tttctttgat | 2940 |
| aatgatagca aatccttcag tggggtcttg gactgtggta actgttccag aatctttcac | 3000 |
| gttgaaaaac ttatgaacac caacttaata ttcataatgg ttgagagcaa agggacttgt | 3060 |
| ccttgtgaca cacgattgct catacaagct gagcagactt ctgacggtcc agatccttgt | 3120 |
| gatatggtta agcaacccag ataccgaaaa gggcctgatg tctgttttga taacaatgcc | 3180 |
| ttggaggatt ataccgactg tggtggtgtt tctggattaa atccctccct gtggtccatc | 3240 |
| ttcggaatcc agtgtgtttt actttggctt ttatctggca gcagacacta ccagttatga | 3300 |
| cccttctaaa accaaatctg catattaaac ttcagaccct gccagaatag gagccctcaa | 3360 |
| ttgcattaaa atagggtaaa ctgcagaatc agcagaactc tagctgggcc catcccatgg | 3420 |
| catcaatctc agactcataa ggcacccact ggctgcatgt cagggtgtca gatcctgaaa | 3480 |
| cttgtgtgaa tgctgcatca tctatgtata acatcagagc aaaattctat acctattcta | 3540 |
| ttggaaaatt tgagaatttg ttgttgcatt gttggtgatt acatgtaaaa gggctcccca | 3600 |
| cacagttgtg tatgaatcac gcaaattgtc ttgattttga cttgctgcaa tccttgtcct | 3660 |
| tttaccaaga aaatctctag agggaaaaaa aaagtctttt ttttccttca ctaattctgc | 3720 |
| tacaaattat ttcctgcttg gagtagttat tattaaaaaa tatatatata gagagagaga | 3780 |
| gagagaatta acattggtgt aatctgtcaa aatagaaata atggcttatt ttctacaaaa | 3840 |
| aa | 3842 |

<210> SEQ ID NO 2
<211> LENGTH: 3057
<212> TYPE: DNA
<213> ORGANISM: Sus scrofa

<400> SEQUENCE: 2

| | |
|---|---:|
| atggctgctg gctgcctgct ggccttgact ctgacacttt tccaatcttt gctgatcgtt | 60 |
| ccctcatcgc aggagccgtt cccgtcggcc gtcactatca agtcatgggt ggataaaatg | 120 |
| caagaagacc ttgtcaccct ggcaaaaaca gcaagtggag tcaatcagct tgtcgatatt | 180 |
| tatgaaaaat accaagattt gtatactgtg aaccaaata atgcacgcca gctggtggaa | 240 |
| attgcagcca gggatattga aaacttctg agcaacagat ctaaagccct ggtgcgccta | 300 |
| gctttggaag cagagaaggt tcaagcagcc accagtggaa gagaggattt tgcaagcaat | 360 |
| gaagttgtct actacaatgc aaaggatgat ctcgatcctg aaaaaaatga cagtgagcca | 420 |
| ggcagccaga ggataaaacc tgttttttatt gatgatgcta attttgggcg acagatatct | 480 |
| tatcagcatg cagcagtcca tattcccacc gacatctatg agggctcaac aattgtgtta | 540 |

-continued

```
aatgaactga actggacaag tgccttagat gaagttttca agaaaaatcg agaggaagat    600
ccctcattat tgtggcaggt gtttggcagt gccacaggcc tggcccggta ttatccagct    660
tctccatggg ttgataacag tagaactcca aacaagattg acctttatga tgtacgaagg    720
agaccatggt acatccaagg agctgcatct cctaaagata tgcttattct ggtcgacgtg    780
agtggaagtg ttagtggttt gacgcttaaa ctgatccgaa catctgtctc tgaaatgttg    840
gaaaccctct cagatgacga ttttgtgaat gtagcttcat ttaacagcaa tgcccaggat    900
gtaagctgtt tcaacaccct tgtccaagca aatgtaagaa ataagaaagt gctgaaagat    960
gcagttaata atatcacagc aaaaggaatc acagattaca agaagggctt tagttttgct   1020
tttgaacaac tgcttaatta taacgtttct agagccaact gcaataagat tatcatgttg   1080
ttcaccgatg gaggagaaga gagagctcag gagatatttg ccaaatacaa caaagacaaa   1140
aaagtacgtg tattcacatt ttcagttggt caacataatt atgacagagg acctattcag   1200
tggatggcct gtgaaaataa aggttattat tatgaaattc cttccattgg agcaatcaga   1260
atcaatactc aggaatattt ggatgttctg gaagaccaa tggttttagc aggagacaaa   1320
gctaagcaag tccagtggac aaacgtgtac ctggatgcac tggaactggg acttgtcatt   1380
actgaactc ttccggtctt caacataacc ggccaaaatg aaaataagac gaacttaaag   1440
aaccagctga ttcttggtgt gatgggagtt gatgtatctt tggaagatat taaaagactg   1500
acaccacgtt ttacactgtg ccccaatggc tattactttg caattgatcc taatggctat   1560
gtttttattac atccaaatct tcagccaaag aaccccaaat ctcaggagcc agtaaccttg   1620
gatttccttg atgcagaatt agagaatgat attaaagtgg agatccgaaa taaaatgata   1680
gatggagaaa gtggagaaaa aacattcaga actctggtta atctcaaga tgagagatat   1740
attgacaaag gaaacaggac atatacatgg actcctgtca atggcacaga ttacagtttg   1800
gccttggtat taccaaccta cagtttttac tatataaaag ccaaaataga agagacaata   1860
actcaggcca gatcaaaaaa gggcaaaatg aaggattcag aaacactgaa gcctgataat   1920
tttgaagaat ctggctatac attcatagca ccaagagact actgcaatga ccttaaaata   1980
tcagataata ataccgaatt tctttttaaac tttaatgagt ttattgatag aaaaactcca   2040
aacaacccgt catgcaacac agatttgatt aatagagtct gctggatgc gggctttaca   2100
aatgaacttg tccaaaatta ctggagtaag cagaaaaaca tcaagggagt gaaagcacgg   2160
tttgttgtaa ctgatggagg gattaccaga gtttatccca agaggctgg agaaaattgg   2220
caagaaaacc cagaaacata tgaggacagc ttctataaaa gaagtctaga taacgataac   2280
tatgttttca ctgctcccta ctttaacaaa agtggacctg gtgcttatga atcaggcatc   2340
atggtaagca aagctgtaga aatatacatc caaggaaaac ttcttaaacc tgcagttgtt   2400
ggaattaaaa ttgatgtaaa ttcctggata gagaatttca ccaaaacatc aatcagggat   2460
ccgtgtgctg gtccagtttg tgattgtaaa agaaacagtg atgtaatgga ttgtgtgatt   2520
ctagatgatg tgggtttct tttgatggca aatcatgatg attatactaa ccagattgga   2580
aggttttttg gagagattga cccaagtttg atgagacacc tggttaatat atcagtttat   2640
gcttttaaca aatcttacga ttatcagtca gtgtgtgagc tggtgctgc accaaaacaa   2700
ggagcaggac atcgctcagc atatgtgcca tcaatagcag acatcttaca cattggctgg   2760
tgggccactg cagctgcatg gtctattcta cagcagtttc tcttgagttt gacctttcca   2820
cgacttcttg aagcagttga gatggaagat gatgacttta ccgcctctct gtcaaagcag   2880
```

-continued

| | |
|---|---|
| agttgcatta ctgaacaaac ccagtatttc tttgataatg atagcaaatc cttcagtggg | 2940 |
| gtcttggact gtggtaactg ttccagaatc tttcacgttg aaaaacttat gaacaccaac | 3000 |
| ttaatattca taatggttga gagcaaaggg acttgtcctt gtgacacacg attgtga | 3057 |

<210> SEQ ID NO 3
<211> LENGTH: 3111
<212> TYPE: DNA
<213> ORGANISM: Sus scrofa

<400> SEQUENCE: 3

| | |
|---|---|
| atggctgctg gctgcctgct ggccttgact ctgacacttt tccaatcttt gctgatcggt | 60 |
| ccctcatcgc aggagccgtt cccgtcggcc gtcactatca agtcatgggt ggataaaatg | 120 |
| caagaagacc ttgtcaccct ggcaaaaaca gcaagtggag tcaatcagct tgtcgatatt | 180 |
| tatgaaaaat accaagattt gtatactgtg aaccaaata atgcacgcca gctggtggaa | 240 |
| attgcagcca gggatattga gaacttctg agcaacagat ctaaagccct ggtgcgccta | 300 |
| gctttggaag cagagaaggt tcaagcagcc accagtggaa gagaggattt tgcaagcaat | 360 |
| gaagttgtct actacaatgc aaaggatgat ctcgatcctg aaaaaaatga cagtgagcca | 420 |
| ggcagccaga ggataaaaacc tgttttattt gatgatgcta attttgggcg acagatatct | 480 |
| tatcagcatg cagcagtcca tattcccacc gacatctatg agggctcaac aattgtgtta | 540 |
| aatgaactga actggacaag tgccttagat gaagttttca gaaaaatcg agaggaagat | 600 |
| ccctcattat tgtggcaggt gtttggcagt gccacaggcc tggcccggta ttatccagct | 660 |
| tctccatggg ttgataacag tagaactcca acaagattg acctttatga tgtacgaagg | 720 |
| agaccatggt acatccaagg agctgcatct cctaaagata tgcttattct ggtcgacgtg | 780 |
| agtggaagtg ttagtggttt gacgcttaaa ctgatccgaa catctgtctc tgaaatgttg | 840 |
| gaaaccctct cagatgacga ttttgtgaat gtagcttcat taacagcaa tgcccaggat | 900 |
| gtaagctgtt tcaacacct tgtccaagca aatgtaagaa ataagaaagt gctgaaagat | 960 |
| gcagttaata atatcacagc aaaaggaatc acagattaca agaagggctt tagttttgct | 1020 |
| tttgaacaac tgcttaatta taacgtttct agagccaact gcaataagat tatcatgttg | 1080 |
| ttcaccgatg gaggagaaga gagagctcag gagatatttg ccaaatacaa caaagacaaa | 1140 |
| aaagtacgtg tattcacatt ttcagttggt caacataatt atgacagagg acctattcag | 1200 |
| tggatggcct gtgaaaataa aggttattat tatgaaattc cttccattgg agcaatcaga | 1260 |
| atcaatactc aggaatattt ggatgttctg ggaagaccaa tggtttagc aggagacaaa | 1320 |
| gctaagcaag tccagtggac aaacgtgtac ctgatgcac tggaactggg acttgtcatt | 1380 |
| actggaactc ttccggtctt caacataacc ggccaaaatg aaaataagac gaacttaaag | 1440 |
| aaccagctga ttcttggtgt gatgggagtt gatgtatctt ggaagatat taaaagactg | 1500 |
| acaccacgtt ttacactgtg ccccaatggc tattactttg caattgatcc taatggctat | 1560 |
| gttttattac atccaaatct tcagccaaag aaccccaaat ctcaggagcc agtaaccttg | 1620 |
| gatttccttg atgcagaatt agagaatgat attaaagtgg agatccgaaa taaaatgata | 1680 |
| gatggagaaa gtggagaaaa aacattcaga actctggtta atctcaaga tgagagatat | 1740 |
| attgacaaag gaacaggac atatacatgg actcctgtca atggcacaga ttacagtttg | 1800 |
| gccttggtat taccaaccta cagttttttac tatataaaag ccaaaataga agagacaata | 1860 |
| actcaggcca gatcaaaaaa gggcaaaatg aaggattcag aaacactgaa gcctgataat | 1920 |
| tttgaagaat ctggctatac attcatagca ccaagagact actgcaatga ccttaaaata | 1980 |

-continued

```
tcagataata ataccgaatt tcttttaaac tttaatgagt ttattgatag aaaaactcca      2040
aacaacccgt catgcaacac agatttgatt aatagagtct tgctggatgc gggctttaca      2100
aatgaacttg tccaaaatta ctggagtaag cagaaaaaca tcaagggagt gaaagcacgg      2160
tttgttgtaa ctgatggagg gattaccaga gtttatccca agaggctgg  agaaaattgg      2220 caagaaaacc cagaaacata tgaggacagc ttctataaaa gaagtctaga taacgataac      2280
tatgttttca ctgctcccta ctttaacaaa agtggacctg gtgcttatga atcaggcatc      2340
atggtaagca aagctgtaga aatatacatc aaggaaaac  ttcttaaacc tgcagttgtt      2400
ggaattaaaa ttgatgtaaa ttcctggata gagaatttca ccaaaacatc aatcagggat      2460
ccgtgtgctg gtccagtttg tgattgtaaa agaaacagtg atgtaatgga ttgtgtgatt      2520
ctagatgatg gtgggtttct tttgatggca aatcatgatg attatactaa ccagattgga      2580
aggttttttg gagagattga cccaagtttg atgagacacc tggttaatat atcagtttat      2640
gcttttaaca aatcttacga ttatcagtca gtgtgtgagc tggtgctgc  accaaaacaa      2700 ggagcaggac atcgctcagc atatgtgcca tcaatagcag acatcttaca cattggctgg      2760
tgggccactg cagctgcatg gtctattcta cagcagtttc tcttgagttt gacctttcca      2820
cgacttcttg aagcagttga gatggaagat gatgacttta ccgcctctct gtcaaagcag      2880
agttgcatta ctgaacaaac ccagtatttc tttgataatg tagcaaatc  cttcagtggg      2940 gtcttggact gtggtaactg ttccagaatc tttcacgttg aaaaactat  gaacaccaac      3000 ttaatattca taatggttga gagcaaaggg acttgtcctt gtgacacacg attgctcata      3060
caagctgagc agacttctga cggtccagat ccttgtgata tggttaagtg a               3111
```

<210> SEQ ID NO 4
<211> LENGTH: 3192
<212> TYPE: DNA
<213> ORGANISM: Sus scrofa

<400> SEQUENCE: 4

```
atggctgctg gctgcctgct ggccttgact ctgacacttt tccaatcttt gctgatcggt       60
ccctcatcgc aggagccgtt cccgtcggcc gtcactatca agtcatgggt ggataaaatg      120
caagaagacc ttgtcaccct ggcaaaaaca gcaagtggag tcaatcagct tgtcgatatt      180
tatgaaaaat accaagattt gtatactgtg aaccaaata  atgcacgcca gctggtggaa      240
attgcagcca gggatattga aaacttctg  agcaacagat ctaaagccct ggtgcgccta      300
gctttggaag cagagaaggt tcaagcagcc caccagtgga gagaggattt tgcaagcaat      360
gaagttgtct actacaatgc aaaggatgat ctcgatcctg aaaaaaatga cagtgagcca      420
ggcagccaga ggataaaacc tgttttatt  gatgatgcta attttgggcg acagatatct      480
tatcagcatg cagcagtcca tattcccacc gacatctatg agggctcaac aattgtgtta      540
aatgaactga actggacaag tgccttagat gaagttttca agaaaaatcg agaggaagat      600
cccctcatta ttgtggcaggt gtttggcagt gccacaggcc tggcccggta ttatccagct      660
tctccatggg ttgataacag tagaactcca aacaagattg acctttatga tgtacgaagg      720
agaccatggt acatccaagg agctgcatct cctaaagata tgcttattct ggtcgacgtg      780
agtggaagtg ttagtggttt gacgcttaaa ctgatccgaa catctgtctc tgaaatgttg      840
gaaaccctct cagatgacga ttttgtgaat gtagcttcat taacagcaa  tgcccaggat      900 gtaagctgtt ttcaacacct tgtccaagca aatgtaagaa ataagaaagt gctgaaagat      960
```

```
gcagttaata atatcacagc aaaaggaatc acagattaca agaagggctt tagttttgct    1020
tttgaacaac tgcttaatta taacgtttct agagccaact gcaataagat tatcatgttg    1080
ttcaccgatg gaggaagaga gagagctcag gagatatttg ccaaatacaa caaagacaaa    1140
aaagtacgtg tattcacatt ttcagttggt caacataatt atgacagagg acctattcag    1200
tggatggcct gtgaaaataa aggttattat tatgaaattc cttccattgg agcaatcaga    1260
atcaatactc aggaatattt ggatgttctg ggaagaccaa tggttttagc aggagacaaa    1320
gctaagcaag tccagtggac aaacgtgtac ctggatgcac tggaactggg acttgtcatt    1380
actggaactc ttccggtctt caacataacc ggccaaaatg aaaataagac gaacttaaag    1440
aaccagctga ttcttggtgt gatgggagtt gatgtatctt ggaagatat taaaagactg    1500 acaccacgtt ttacactgtg ccccaatggc tattactttg caattgatcc taatggctat    1560
gttttattac atccaaatct tcagccaaag aaccccaaat ctcaggagcc agtaaccttg    1620
gatttccttg atgcagaatt agagaatgat attaaagtgg atccgaaaa taaaatgata    1680 gatggagaaa gtggagaaaa aacattcaga actctggtta aatctcaaga tgagagatat    1740
attgacaaag gaaacaggac atatacatgg actcctgtca atggcacaga ttacagtttg    1800
gccttggtat taccaaccta cagttttttac tatataaaag ccaaaataga agagacaata    1860
actcaggcca gatcaaaaaa gggcaaaatg aaggattcag aaacactgaa gcctgataat    1920
tttgaagaat ctggctatac attcatagca ccaagagact actgcaatga ccttaaaata    1980
tcagataata taccgaattt cttttaaac tttaatgagt ttattgatag aaaaactcca    2040
aacaacccgt catgcaacac agatttgatt aatagagtct tgctggatgc gggctttaca    2100
aatgaacttg tccaaaatta ctggagtaag cagaaaaaca tcaagggagt gaaagcacgg    2160
tttgttgtaa ctgatggagg gattaccaga gtttatccca agaggctgg agaaaattgg    2220 caagaaaacc cagaaacata tgaggacagc ttctataaaa gaagtctaga taacgataac    2280
tatgttttca ctgctcccta ctttaacaaa agtggacctg gtgcttatga atcaggcatc    2340
atggtaagca aagctgtaga aatatacatc aaggaaaaac ttcttaaacc tgcagttgtt    2400
ggaattaaaa ttgatgtaaa ttcctggata gagaatttca ccaaaacatc aatcagggat    2460
ccgtgtgctg gtccagtttg tgattgtaaa gaaacagtg atgtaatgga ttgtgtgatt    2520
ctagatgatg gtgggtttct tttgatggca aatcatgatg attatactaa ccagattgga    2580 aggtttttg gagagattga cccaagtttg atgagacacc tggttaatat atcagtttat    2640
gcttttaaca aatcttacga ttatcagtca gtgtgtgagc ctggtgctgc accaaaacaa    2700
ggagcaggac atcgctcagc atatgtgcca tcaatagcag acatcttaca cattggctgg    2760
tgggccactg cagctgcatg gtctattcta cagcagtttc tcttgagttt gacctttcca    2820
cgacttcttg aagcagttga gatggaagat gatgacttta ccgcctctct gtcaaagcag    2880
agttgcatta ctgaacaaac ccagtatttc tttgataatg atagcaaatc cttcagtggg    2940
gtcttggact gtggtaactg ttccagaatc tttcacgttg aaaaacttat gaacaccaac    3000
ttaatattca taatggttga gagcaaaggg acttgtcctt gtgacacacg attgctcata    3060
caagctgagc agacttctga cggtccagat ccttgtgata tggttaagca acccagatac    3120
cgaaaagggc ctgatgtctg ttttgataac aatgccttgg aggattatac cgactgtggt    3180
ggtgtttctt ga                                                       3192

<210> SEQ ID NO 5
<211> LENGTH: 1091
```

```
<212> TYPE: PRT
<213> ORGANISM: Sus scrofa

<400> SEQUENCE: 5
```

| | | | | | | | | | | | | | | |
|---|---|---|---|---|---|---|---|---|---|---|---|---|---|---|
| Met | Ala | Ala | Gly | Cys | Leu | Leu | Ala | Leu | Thr | Leu | Thr | Leu | Phe | Gln | Ser |
| 1 | | | | 5 | | | | | 10 | | | | | 15 | |
| Leu | Leu | Ile | Gly | Pro | Ser | Ser | Gln | Glu | Pro | Phe | Pro | Ser | Ala | Val | Thr |
| | | | | 20 | | | | | 25 | | | | | 30 | |
| Ile | Lys | Ser | Trp | Val | Asp | Lys | Met | Gln | Glu | Asp | Leu | Val | Thr | Leu | Ala |
| | | | 35 | | | | | 40 | | | | | 45 | | |
| Lys | Thr | Ala | Ser | Gly | Val | Asn | Gln | Leu | Val | Asp | Ile | Tyr | Glu | Lys | Tyr |
| | 50 | | | | | 55 | | | | | 60 | | | | |
| Gln | Asp | Leu | Tyr | Thr | Val | Glu | Pro | Asn | Asn | Ala | Arg | Gln | Leu | Val | Glu |
| 65 | | | | | 70 | | | | | 75 | | | | | 80 |
| Ile | Ala | Ala | Arg | Asp | Ile | Glu | Lys | Leu | Leu | Ser | Asn | Arg | Ser | Lys | Ala |
| | | | | 85 | | | | | 90 | | | | | 95 | |
| Leu | Val | Arg | Leu | Ala | Leu | Glu | Ala | Glu | Lys | Val | Gln | Ala | Ala | His | Gln |
| | | | | 100 | | | | | 105 | | | | | 110 | |
| Trp | Arg | Glu | Asp | Phe | Ala | Ser | Asn | Glu | Val | Val | Tyr | Tyr | Asn | Ala | Lys |
| | | | 115 | | | | | 120 | | | | | 125 | | |
| Asp | Asp | Leu | Asp | Pro | Glu | Lys | Asn | Asp | Ser | Glu | Pro | Gly | Ser | Gln | Arg |
| 130 | | | | | 135 | | | | | 140 | | | | | |
| Ile | Lys | Pro | Val | Phe | Ile | Asp | Asp | Ala | Asn | Phe | Gly | Arg | Gln | Ile | Ser |
| 145 | | | | | 150 | | | | | 155 | | | | | 160 |
| Tyr | Gln | His | Ala | Ala | Val | His | Ile | Pro | Thr | Asp | Ile | Tyr | Glu | Gly | Ser |
| | | | | 165 | | | | | 170 | | | | | 175 | |
| Thr | Ile | Val | Leu | Asn | Glu | Leu | Asn | Trp | Thr | Ser | Ala | Leu | Asp | Glu | Val |
| | | | 180 | | | | | 185 | | | | | 190 | | |
| Phe | Lys | Lys | Asn | Arg | Glu | Glu | Asp | Pro | Ser | Leu | Leu | Trp | Gln | Val | Phe |
| | | | 195 | | | | | 200 | | | | | 205 | | |
| Gly | Ser | Ala | Thr | Gly | Leu | Ala | Arg | Tyr | Tyr | Pro | Ala | Ser | Pro | Trp | Val |
| | 210 | | | | | 215 | | | | | 220 | | | | |
| Asp | Asn | Ser | Arg | Thr | Pro | Asn | Lys | Ile | Asp | Leu | Tyr | Asp | Val | Arg | Arg |
| 225 | | | | | 230 | | | | | 235 | | | | | 240 |
| Arg | Pro | Trp | Tyr | Ile | Gln | Gly | Ala | Ala | Ser | Pro | Lys | Asp | Met | Leu | Ile |
| | | | | 245 | | | | | 250 | | | | | 255 | |
| Leu | Val | Asp | Val | Ser | Gly | Ser | Val | Ser | Gly | Leu | Thr | Leu | Lys | Leu | Ile |
| | | | | 260 | | | | | 265 | | | | | 270 | |
| Arg | Thr | Ser | Val | Ser | Glu | Met | Leu | Glu | Thr | Leu | Ser | Asp | Asp | Asp | Phe |
| | | 275 | | | | | 280 | | | | | 285 | | | |
| Val | Asn | Val | Ala | Ser | Phe | Asn | Ser | Asn | Ala | Gln | Asp | Val | Ser | Cys | Phe |
| | 290 | | | | | 295 | | | | | 300 | | | | |
| Gln | His | Leu | Val | Gln | Ala | Asn | Val | Arg | Asn | Lys | Lys | Val | Leu | Lys | Asp |
| 305 | | | | | 310 | | | | | 315 | | | | | 320 |
| Ala | Val | Asn | Asn | Ile | Thr | Ala | Lys | Gly | Ile | Thr | Asp | Tyr | Lys | Lys | Gly |
| | | | | 325 | | | | | 330 | | | | | 335 | |
| Phe | Ser | Phe | Ala | Phe | Glu | Gln | Leu | Leu | Asn | Tyr | Asn | Val | Ser | Arg | Ala |
| | | | | 340 | | | | | 345 | | | | | 350 | |
| Asn | Cys | Asn | Lys | Ile | Ile | Met | Leu | Phe | Thr | Asp | Gly | Gly | Glu | Glu | Arg |
| | | | 355 | | | | | 360 | | | | | 365 | | |
| Ala | Gln | Glu | Ile | Phe | Ala | Lys | Tyr | Asn | Lys | Asp | Lys | Lys | Val | Arg | Val |
| | | 370 | | | | | 375 | | | | | 380 | | | |
| Phe | Thr | Phe | Ser | Val | Gly | Gln | His | Asn | Tyr | Asp | Arg | Gly | Pro | Ile | Gln |
| 385 | | | | | 390 | | | | | 395 | | | | | 400 |

```
Trp Met Ala Cys Glu Asn Lys Gly Tyr Tyr Glu Ile Pro Ser Ile
            405                 410                 415
Gly Ala Ile Arg Ile Asn Thr Gln Glu Tyr Leu Asp Val Leu Gly Arg
        420                 425                 430
Pro Met Val Leu Ala Gly Asp Lys Ala Lys Gln Val Gln Trp Thr Asn
            435                 440                 445
Val Tyr Leu Asp Ala Leu Glu Leu Gly Leu Val Ile Thr Gly Thr Leu
    450                 455                 460
Pro Val Phe Asn Ile Thr Gly Gln Asn Glu Asn Lys Thr Asn Leu Lys
465                 470                 475                 480
Asn Gln Leu Ile Leu Gly Val Met Gly Val Asp Val Ser Leu Glu Asp
                485                 490                 495
Ile Lys Arg Leu Thr Pro Arg Phe Thr Leu Cys Pro Asn Gly Tyr Tyr
            500                 505                 510
Phe Ala Ile Asp Pro Asn Gly Tyr Val Leu Leu His Pro Asn Leu Gln
            515                 520                 525
Pro Lys Asn Pro Lys Ser Gln Glu Pro Val Thr Leu Asp Phe Leu Asp
530                 535                 540
Ala Glu Leu Glu Asn Asp Ile Lys Val Glu Ile Arg Asn Lys Met Ile
545                 550                 555                 560
Asp Gly Glu Ser Gly Glu Lys Thr Phe Arg Thr Leu Val Lys Ser Gln
                565                 570                 575
Asp Glu Arg Tyr Ile Asp Lys Gly Asn Arg Thr Tyr Thr Trp Thr Pro
            580                 585                 590
Val Asn Gly Thr Asp Tyr Ser Leu Ala Leu Val Leu Pro Thr Tyr Ser
            595                 600                 605
Phe Tyr Tyr Ile Lys Ala Lys Ile Glu Glu Thr Ile Thr Gln Ala Arg
            610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
                645                 650                 655
Asp Leu Lys Ile Ser Asp Asn Asn Thr Glu Phe Leu Leu Asn Phe Asn
            660                 665                 670
Glu Phe Ile Asp Arg Lys Thr Pro Asn Pro Ser Cys Asn Thr Asp
            675                 680                 685
Leu Ile Asn Arg Val Leu Leu Asp Ala Gly Phe Thr Asn Glu Leu Val
        690                 695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
            755                 760                 765
Asn Lys Ser Gly Pro Gly Ala Tyr Glu Ser Gly Ile Met Val Ser Lys
            770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
```

```
Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Phe Gly
            850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Trp Ser
            915                 920                 925

Ile Leu Gln Gln Phe Leu Leu Ser Leu Thr Phe Pro Arg Leu Leu Glu
            930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
            965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asp Pro Cys Asp Met Val Lys Gln Pro Arg Tyr
1025                1030                1035                1040

Arg Lys Gly Pro Asp Val Cys Phe Asp Asn Asn Ala Leu Glu Asp Tyr
                1045                1050                1055

Thr Asp Cys Gly Gly Val Ser Gly Leu Asn Pro Ser Leu Trp Ser Ile
            1060                1065                1070

Phe Gly Ile Gln Cys Val Leu Leu Trp Leu Leu Ser Gly Ser Arg His
            1075                1080                1085

Tyr Gln Leu
    1090

<210> SEQ ID NO 6
<211> LENGTH: 1018
<212> TYPE: PRT
<213> ORGANISM: Sus scrofa

<400> SEQUENCE: 6

Met Ala Ala Gly Cys Leu Leu Ala Leu Thr Leu Thr Leu Phe Gln Ser
1               5                   10                  15

Leu Leu Ile Gly Pro Ser Ser Gln Glu Pro Phe Pro Ser Ala Val Thr
            20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
        50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95
```

-continued

```
Leu Val Arg Leu Ala Leu Glu Ala Glu Lys Val Gln Ala Ala His Gln
        100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
        130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                    165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                    245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
        290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                    325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Ala Lys Tyr Asn Lys Asp Lys Lys Val Arg Val
        370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Glu Ile Pro Ser Ile
                    405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
        450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                    485                 490                 495

Ile Lys Arg Leu Thr Pro Arg Phe Thr Leu Cys Pro Asn Gly Tyr Tyr
            500                 505                 510
```

-continued

```
Phe Ala Ile Asp Pro Asn Gly Tyr Val Leu Leu His Pro Asn Leu Gln
        515                 520                 525
Pro Lys Asn Pro Lys Ser Gln Glu Pro Val Thr Leu Asp Phe Leu Asp
        530                 535                 540
Ala Glu Leu Glu Asn Asp Ile Lys Val Glu Ile Arg Asn Lys Met Ile
545                 550                 555                 560
Asp Gly Glu Ser Gly Glu Lys Thr Phe Arg Thr Leu Val Lys Ser Gln
                565                 570                 575
Asp Glu Arg Tyr Ile Asp Lys Gly Asn Arg Thr Tyr Thr Trp Thr Pro
            580                 585                 590
Val Asn Gly Thr Asp Tyr Ser Leu Ala Leu Val Leu Pro Thr Tyr Ser
        595                 600                 605
Phe Tyr Tyr Ile Lys Ala Lys Ile Glu Thr Ile Thr Gln Ala Arg
        610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
                645                 650                 655
Asp Leu Lys Ile Ser Asp Asn Asn Thr Glu Phe Leu Leu Asn Phe Asn
            660                 665                 670
Glu Phe Ile Asp Arg Lys Thr Pro Asn Asn Pro Ser Cys Asn Thr Asp
        675                 680                 685
Leu Ile Asn Arg Val Leu Leu Asp Ala Gly Phe Thr Asn Glu Leu Val
        690                 695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
        755                 760                 765
Asn Lys Ser Gly Pro Gly Ala Tyr Glu Ser Gly Ile Met Val Ser Lys
        770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
            820                 825                 830
Ser Asp Val Met Asp Cys Val Ile Leu Asp Asp Gly Gly Phe Leu Leu
        835                 840                 845
Met Ala Asn His Asp Asp Tyr Thr Asn Gln Ile Gly Arg Phe Phe Gly
        850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Ile
            900                 905                 910
Ala Asp Ile Leu His Ile Gly Trp Trp Ala Thr Ala Ala Ala Trp Ser
        915                 920                 925
Ile Leu Gln Gln Phe Leu Leu Ser Leu Thr Phe Pro Arg Leu Leu Glu
```

```
                    930              935              940
Ala Val Glu Met Glu Asp Asp Phe Thr Ala Ser Leu Ser Lys Gln
945                 950              955                 960

Ser Cys Ile Thr Glu Gln Thr Gln Tyr Phe Phe Asp Asn Asp Ser Lys
                965              970              975

Ser Phe Ser Gly Val Leu Asp Cys Gly Asn Cys Ser Arg Ile Phe His
            980              985              990

Val Glu Lys Leu Met Asn Thr Asn Leu Ile Phe Ile Met Val Glu Ser
            995             1000             1005

Lys Gly Thr Cys Pro Cys Asp Thr Arg Leu
    1010            1015

<210> SEQ ID NO 7
<211> LENGTH: 1036
<212> TYPE: PRT
<213> ORGANISM: Sus scrofa

<400> SEQUENCE: 7

Met Ala Ala Gly Cys Leu Leu Ala Leu Thr Leu Thr Leu Phe Gln Ser
 1               5                  10                  15

Leu Leu Ile Gly Pro Ser Ser Gln Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285
```

-continued

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Ala Lys Tyr Asn Lys Asp Lys Lys Val Arg Val
    370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Ile Glu Glu Thr Ile Thr Gln Ala Arg
    610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Thr Asp
        675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg

```
                705                 710                 715                 720
Phe Val Val Thr Asp Gly Gly Ile Thr Arg Val Tyr Pro Lys Glu Ala
                    725                 730                 735
Gly Glu Asn Trp Gln Glu Asn Pro Glu Thr Tyr Glu Asp Ser Phe Tyr
                740                 745                 750
Lys Arg Ser Leu Asp Asn Asp Asn Tyr Val Phe Thr Ala Pro Tyr Phe
                755                 760                 765
Asn Lys Ser Gly Pro Gly Ala Tyr Glu Ser Gly Ile Met Val Ser Lys
                770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                    805                 810                 815
Ser Ile Arg Asp Pro Cys Ala Gly Pro Val Cys Asp Cys Lys Arg Asn
                820                 825                 830
Ser Asp Val Met Asp Cys Val Ile Leu Asp Asp Gly Gly Phe Leu Leu
                835                 840                 845
Met Ala Asn His Asp Asp Tyr Thr Asn Gln Ile Gly Arg Phe Phe Gly
850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                    885                 890                 895
Ala Pro Lys Gln Gly Ala Gly His Arg Ser Ala Tyr Val Pro Ser Ile
                900                 905                 910
Ala Asp Ile Leu His Ile Gly Trp Trp Ala Thr Ala Ala Trp Ser
                915                 920                 925
Ile Leu Gln Gln Phe Leu Leu Ser Leu Thr Phe Pro Arg Leu Leu Glu
                930                 935                 940
Ala Val Glu Met Glu Asp Asp Phe Thr Ala Ser Leu Ser Lys Gln
945                 950                 955                 960
Ser Cys Ile Thr Glu Gln Thr Gln Tyr Phe Phe Asp Asn Asp Ser Lys
                    965                 970                 975
Ser Phe Ser Gly Val Leu Asp Cys Gly Asn Cys Ser Arg Ile Phe His
                980                 985                 990
Val Glu Lys Leu Met Asn Thr Asn Leu Ile Phe Ile Met Val Glu Ser
            995                 1000                1005
Lys Gly Thr Cys Pro Cys Asp Thr Arg Leu Leu Ile Gln Ala Glu Gln
    1010                1015                1020
Thr Ser Asp Gly Pro Asp Pro Cys Asp Met Val Lys
1025                1030                1035

<210> SEQ ID NO 8
<211> LENGTH: 1063
<212> TYPE: PRT
<213> ORGANISM: Sus scrofa

<400> SEQUENCE: 8

Met Ala Ala Gly Cys Leu Leu Ala Leu Thr Leu Thr Leu Phe Gln Ser
1               5                   10                  15
Leu Leu Ile Gly Pro Ser Ser Gln Glu Pro Phe Pro Ser Ala Val Thr
                20                  25                  30
Ile Lys Ser Trp Val Asp Lys Met Gln Glu Asp Leu Val Thr Leu Ala
                35                  40                  45
```

```
Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Ala Lys Tyr Asn Lys Asp Lys Lys Val Arg Val
    370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
```

-continued

```
           465                 470                 475                 480
     Asn Gln Leu Ile Leu Gly Val Met Gly Val Asp Val Ser Leu Glu Asp
                     485                 490                 495
     Ile Lys Arg Leu Thr Pro Arg Phe Thr Leu Cys Pro Asn Gly Tyr Tyr
                 500                 505                 510
     Phe Ala Ile Asp Pro Asn Gly Tyr Val Leu Leu His Pro Asn Leu Gln
                 515                 520                 525
     Pro Lys Asn Pro Lys Ser Gln Glu Pro Val Thr Leu Asp Phe Leu Asp
                 530                 535                 540
     Ala Glu Leu Glu Asn Asp Ile Lys Val Glu Ile Arg Asn Lys Met Ile
     545                 550                 555                 560
     Asp Gly Glu Ser Gly Glu Lys Thr Phe Arg Thr Leu Val Lys Ser Gln
                         565                 570                 575
     Asp Glu Arg Tyr Ile Asp Lys Gly Asn Arg Thr Tyr Thr Trp Thr Pro
                     580                 585                 590
     Val Asn Gly Thr Asp Tyr Ser Leu Ala Leu Val Leu Pro Thr Tyr Ser
                     595                 600                 605
     Phe Tyr Tyr Ile Lys Ala Lys Ile Glu Glu Thr Ile Thr Gln Ala Arg
                 610                 615                 620
     Ser Lys Lys Gly Lys Met Lys Asp Ser Glu Thr Leu Lys Pro Asp Asn
     625                 630                 635                 640
     Phe Glu Glu Ser Gly Tyr Thr Phe Ile Ala Pro Arg Asp Tyr Cys Asn
                         645                 650                 655
     Asp Leu Lys Ile Ser Asp Asn Asn Thr Glu Phe Leu Leu Asn Phe Asn
                     660                 665                 670
     Glu Phe Ile Asp Arg Lys Thr Pro Asn Asn Pro Ser Cys Asn Thr Asp
                     675                 680                 685
     Leu Ile Asn Arg Val Leu Leu Asp Ala Gly Phe Thr Asn Glu Leu Val
                 690                 695                 700
     Gln Asn Tyr Trp Ser Lys Gln Lys Asn Ile Lys Gly Val Lys Ala Arg
     705                 710                 715                 720
     Phe Val Val Thr Asp Gly Gly Ile Thr Arg Val Tyr Pro Lys Glu Ala
                         725                 730                 735
     Gly Glu Asn Trp Gln Glu Asn Pro Glu Thr Tyr Glu Asp Ser Phe Tyr
                     740                 745                 750
     Lys Arg Ser Leu Asp Asn Asp Asn Tyr Val Phe Thr Ala Pro Tyr Phe
                 755                 760                 765
     Asn Lys Ser Gly Pro Gly Ala Tyr Glu Ser Gly Ile Met Val Ser Lys
                 770                 775                 780
     Ala Val Glu Ile Tyr Ile Gln Gly Lys Leu Leu Lys Pro Ala Val Val
     785                 790                 795                 800
     Gly Ile Lys Ile Asp Val Asn Ser Trp Ile Glu Asn Phe Thr Lys Thr
                         805                 810                 815
     Ser Ile Arg Asp Pro Cys Ala Gly Pro Val Cys Asp Cys Lys Arg Asn
                     820                 825                 830
     Ser Asp Val Met Asp Cys Val Ile Leu Asp Asp Gly Gly Phe Leu Leu
                     835                 840                 845
     Met Ala Asn His Asp Asp Tyr Thr Asn Gln Ile Gly Arg Phe Phe Gly
                 850                 855                 860
     Glu Ile Asp Pro Ser Leu Met Arg His Leu Val Asn Ile Ser Val Tyr
     865                 870                 875                 880
     Ala Phe Asn Lys Ser Tyr Asp Tyr Gln Ser Val Cys Glu Pro Gly Ala
                         885                 890                 895
```

```
Ala Pro Lys Gln Gly Ala Gly His Arg Ser Ala Tyr Val Pro Ser Ile
            900                 905                 910
Ala Asp Ile Leu His Ile Gly Trp Trp Ala Thr Ala Ala Trp Ser
            915                 920                 925
Ile Leu Gln Gln Phe Leu Leu Ser Leu Thr Phe Pro Arg Leu Leu Glu
        930                 935                 940
Ala Val Glu Met Glu Asp Asp Asp Phe Thr Ala Ser Leu Ser Lys Gln
945                 950                 955                 960
Ser Cys Ile Thr Glu Gln Thr Gln Tyr Phe Phe Asp Asn Asp Ser Lys
                965                 970                 975
Ser Phe Ser Gly Val Leu Asp Cys Gly Asn Cys Ser Arg Ile Phe His
            980                 985                 990
Val Glu Lys Leu Met Asn Thr Asn Leu Ile Phe Ile Met Val Glu Ser
            995                 1000                1005
Lys Gly Thr Cys Pro Cys Asp Thr Arg Leu Leu Ile Gln Ala Glu Gln
        1010                1015                1020
Thr Ser Asp Gly Pro Asp Pro Cys Asp Met Val Lys Gln Pro Arg Tyr
1025                1030                1035                1040
Arg Lys Gly Pro Asp Val Cys Phe Asp Asn Asn Ala Leu Glu Asp Tyr
                1045                1050                1055
Thr Asp Cys Gly Gly Val Ser
            1060

<210> SEQ ID NO 9
<211> LENGTH: 1069
<212> TYPE: PRT
<213> ORGANISM: Sus scrofa

<400> SEQUENCE: 9

Met Ala Ala Gly Cys Leu Leu Ala Leu Thr Leu Thr Leu Phe Gln Ser
1               5                   10                  15
Leu Leu Ile Gly Pro Ser Ser Gln Glu Pro Phe Pro Ser Ala Val Thr
            20                  25                  30
Ile Lys Ser Trp Val Asp Lys Met Gln Glu Asp Leu Val Thr Leu Ala
        35                  40                  45
Lys Thr Ala Ser Gly Val Asn Gln Leu Val Asp Ile Tyr Glu Lys Tyr
    50                  55                  60
Gln Asp Leu Tyr Thr Val Glu Pro Asn Asn Ala Arg Gln Leu Val Glu
65                  70                  75                  80
Ile Ala Ala Arg Asp Ile Glu Lys Leu Leu Ser Asn Arg Ser Lys Ala
                85                  90                  95
Leu Val Arg Leu Ala Leu Glu Ala Glu Lys Val Gln Ala Ala His Gln
            100                 105                 110
Trp Arg Glu Asp Phe Ala Ser Asn Glu Val Val Tyr Tyr Asn Ala Lys
        115                 120                 125
Asp Asp Leu Asp Pro Glu Lys Asn Asp Ser Glu Pro Gly Ser Gln Arg
    130                 135                 140
Ile Lys Pro Val Phe Ile Asp Asp Ala Asn Phe Gly Arg Gln Ile Ser
145                 150                 155                 160
Tyr Gln His Ala Ala Val His Ile Pro Thr Asp Ile Tyr Glu Gly Ser
                165                 170                 175
Thr Ile Val Leu Asn Glu Leu Asn Trp Thr Ser Ala Leu Asp Glu Val
            180                 185                 190
Phe Lys Lys Asn Arg Glu Glu Asp Pro Ser Leu Leu Trp Gln Val Phe
```

-continued

```
               195                 200                 205
Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
                260                 265                 270

Arg Thr Ser Val Ser Glu Met Leu Glu Thr Leu Ser Asp Asp Asp Phe
            275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
                340                 345                 350

Asn Cys Asn Lys Ile Ile Met Leu Phe Thr Asp Gly Gly Glu Glu Arg
            355                 360                 365

Ala Gln Glu Ile Phe Ala Lys Tyr Asn Lys Asp Lys Lys Val Arg Val
    370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
            515                 520                 525

Pro Lys Asn Pro Lys Ser Gln Glu Pro Val Thr Leu Asp Phe Leu Asp
530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
    595                 600                 605

Phe Tyr Tyr Ile Lys Ala Lys Ile Glu Glu Thr Ile Thr Gln Ala Arg
610                 615                 620
```

-continued

```
Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
            645                 650                 655

Asp Leu Lys Ile Ser Asp Asn Asn Thr Glu Phe Leu Leu Asn Phe Asn
        660                 665                 670

Glu Phe Ile Asp Arg Lys Thr Pro Asn Asn Pro Ser Cys Asn Thr Asp
            675                 680                 685

Leu Ile Asn Arg Val Leu Leu Asp Ala Gly Phe Thr Asn Glu Leu Val
        690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
            725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
        770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
            805                 810                 815

Ser Ile Arg Asp Pro Cys Ala Gly Pro Val Cys Asp Cys Lys Arg Asn
        820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
            885                 890                 895

Ala Pro Lys Gln Gly Ala Gly His Arg Ser Ala Tyr Val Pro Ser Ile
        900                 905                 910

Ala Asp Ile Leu His Ile Gly Trp Trp Ala Thr Ala Ala Trp Ser
        915                 920                 925

Ile Leu Gln Gln Phe Leu Leu Ser Leu Thr Phe Pro Arg Leu Leu Glu
        930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Asp Asn Asp Ser Lys
            965                 970                 975

Ser Phe Ser Gly Val Leu Asp Cys Gly Asn Cys Ser Arg Ile Phe His
        980                 985                 990

Val Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asp Pro Cys Asp Met Val Lys Gln Pro Arg Tyr
1025                1030                1035                1040
```

Arg Lys Gly Pro Asp Val Cys Phe Asp Asn Asn Ala Leu Glu Asp Tyr
        1045                1050                1055

Thr Asp Cys Gly Gly Val Ser His His His His His
        1060                1065

<210> SEQ ID NO 10
<211> LENGTH: 3055
<212> TYPE: DNA
<213> ORGANISM: Homo sapiens

<400> SEQUENCE: 10

| | | | | | |
|---|---|---|---|---|---|
| atggctgctg | gctgcctgct | ggccttgact | ctgacacttt | tccaatcttt | gctcatcggc | 60 |
| ccctcgtcgg | aggagccgtt | cccttcggcc | gtcactatca | aatcatgggt | ggataagatg | 120 |
| caagaagacc | ttgtcacact | ggcaaaaaca | gcaagtggag | tcaatcagct | tgttgatatt | 180 |
| tatgagaaat | atcaagattt | gtatactgtg | aaccaaata | atgcacgcca | gctggtagaa | 240 |
| attgcagcca | gggatattga | gaaacttctg | agcaacagat | ctaaagccct | ggtgagcctg | 300 |
| gcattggaag | cggagaaagt | tcaagcagct | caccagtgga | gagaagattt | tgcaagcaat | 360 |
| gaagttgtct | actacaatgc | aaaggatgat | ctcgatcctg | agaaaaatga | cagtgagcca | 420 |
| ggcagccaga | ggataaaacc | tgttttcatt | gaagatgcta | attttggacg | acaaatatct | 480 |
| tatcagcacg | cagcagtcca | tattcctact | gacatctatg | agggctcaac | aattgtgtta | 540 |
| aatgaactca | actggacaag | tgccttagat | gaagttttca | aaagaatcg | cgaggaagac | 600 |
| ccttcattat | tgtggcaggt | ttttggcagt | gccactggcc | tagctcgata | ttatccagct | 660 |
| tcaccatggg | ttgataatag | tagaactcca | aataagattg | acctttatga | tgtacgcaga | 720 |
| agaccatggt | acatccaagg | agctgcatct | cctaaagaca | tgcttattct | ggtggatgtg | 780 |
| agtggaagtg | ttagtggatt | gacacttaaa | ctgatccgaa | catctgtctc | cgaaatgtta | 840 |
| gaaaccctct | cagatgatga | tttcgtgaat | gtagcttcat | taacagcaa | tgctcaggat | 900 |
| gtaagctgtt | ttcagcacct | tgtccaagca | aatgtaagaa | ataaaaagt | gttgaaagac | 960 |
| gcggtgaata | atatcacagc | caaggaatt | acagattata | agaagggctt | tagttttgct | 1020 |
| tttgaacagc | tgcttaatta | taatgtttcc | agagcaaact | gcaataagat | tattatgcta | 1080 |
| ttcacggatg | gaggagaaga | gagagcccag | gagatattta | acaaatacaa | taaagataaa | 1140 |
| aaagtacgtg | tattcaggtt | ttcagttggt | caacacaatt | atgagagagg | acctattcag | 1200 |
| tggatggcct | gtgaaaacaa | aggttattat | tatgaaattc | cttccattgg | tgcaataaga | 1260 |
| atcaatactc | aggaatattt | ggatgttttg | ggaagaccaa | tggttttagc | aggagacaaa | 1320 |
| gctaagcaag | tccaatggac | aaatgtgtac | ctggatgcat | tggaactggg | acttgtcatt | 1380 |
| actggaactc | ttccggtctt | caacataacc | ggccaatttg | aaaataagac | aaacttaaag | 1440 |
| aaccagctga | ttcttggtgt | gatgggagta | gatgtgtctt | tggaagatat | taaaagactg | 1500 |
| acaccacgtt | ttacactgtg | ccccaatggg | tattactttg | caatcgatcc | taatggttat | 1560 |
| gttttattac | atccaaatct | tcagccaaag | aaccccaaat | ctcaggagcc | agtaacattg | 1620 |
| gatttccttg | atgcagagtt | agaatgat | attaaagtgg | agattcgaaa | taagatgatt | 1680 |
| gatgggaaa | gtggagaaaa | aacattcaga | actctggtta | aatctcaaga | tgagagatat | 1740 |
| attgacaaag | gaacaggac | atacacatgg | acacctgtca | atggcacaga | ttacagtttg | 1800 |
| gccttggtat | taccaaccta | cagtttttac | tatataaaag | ccaaactaga | agagacaata | 1860 |
| actcaggcca | gatcaaaaaa | gggcaaaatg | aaggattcgg | aaaccctgaa | gccagataat | 1920 |
| tttgaagaat | ctggctatac | attcatagca | ccaagagatt | actgcaatga | cctgaaaata | 1980 |

-continued

```
tcggataata acactgaatt tcttttaaat ttcaacgagt ttattgatag aaaaactcca    2040
aacaacccat catgtaacgc ggatttgatt aatagagtct tgcttgatgc aggctttaca    2100
aatgaacttg tccaaaatta ctggagtaag cagaaaaata tcaagggagt gaaagcacga    2160
tttgttgtga ctgatggtgg gattaccaga gtttatccca agaggctgg agaaaattgg     2220 caagaaaacc cagagacata tgaggacagc ttctataaaa ggagcctaga taatgataac    2280
tatgttttca ctgctcccta ctttaacaaa agtggacctg gtgcctatga atcgggcatt    2340
atggtaagca aagctgtaga aatatatatt caagggaaac ttcttaaacc tgcagttgtt    2400
ggaattaaaa ttgatgtaaa ttcctggata gagaatttca ccaaaacctc aatcagagat    2460
ccgtgtgctg gtccagtttg tgactgcaaa agaaacagtg acgtaatgga ttgtgtgatt    2520
ctggatgatg gtgggtttct tctgatggca aatcatgatg attatactaa tcagattgga    2580 agatttttg gagagattga tcccagcttg atgagacacc tggttaatat atcagtttat     2640
gcttttaaca aatcttatga ttatcagtca gtatgtgagc ccggtgctgc accaaaacaa    2700
ggagcaggac atcgctcagc atatgtgcca tcagtagcag acatattaca aattggctgg    2760
tgggccactg ctgctgcctg gtctattcta cagcagtttc tcttgagttt gacctttcca    2820
cgactccttg aggcagttga gatggaggat gatgacttca cggcctccct gtccaagcag    2880
agctgcatta ctgaacaaac ccagtatttc ttcgataacg acagtaaatc attcagtggt    2940
gtattagact gtggaaactg ttccagaatc tttcatggag aaaagcttat gaacaccaac    3000
ttaatattca taatggttga gagcaaaggg acatgtccat gtgacacacg actgc         3055
```

<210> SEQ ID NO 11
<211> LENGTH: 3109
<212> TYPE: DNA
<213> ORGANISM: Homo sapiens

<400> SEQUENCE: 11

```
atggctgctg gctgcctgct ggccttgact ctgacacttt tccaatcttt gctcatcggc      60
ccctcgtcgg aggagccgtt cccttcggcc gtcactatca aatcatgggt ggataagatg     120
caagaagacc ttgtcacact ggcaaaaaca gcaagtggag tcaatcagct tgttgatatt     180
tatgagaaat atcaagattt gtatactgtg gaaccaaata tgcacgcca gctggtagaa      240 attgcagcca gggatattga gaaacttctg agcaacagat ctaaagccct ggtgagcctg     300
gcattggaag cggagaaagt tcaagcagct caccagtgga gagaagattt tgcaagcaat    360
gaagttgtct actacaatgc aaaggatgat ctcgatcctg agaaaaatga cagtgagcca     420
ggcagccaga ggataaaacc tgttttcatt gaagatgcta attttggacg acaaatatct    480
tatcagcacg cagcagtcca tattcctact gacatctatg agggctcaac aattgtgtta    540
aatgaactca actggacaag tgccttagat gaagttttca aaaagaatcg cgaggaagac    600
ccttcattat tgtggcaggt ttttggcagt gccactggcc tagctcgata ttatccagct    660
tcaccatggg ttgataatag tagaactcca aataagattg acctttatga tgtacgcaga    720
agaccatggt acatccaagg agctgcatct cctaaagaca tgcttattct ggtggatgtg    780
agtggaagtg ttagtggatt gacacttaaa ctgatccgaa catctgtctc cgaaatgtta    840
gaaaccctct cagatgatga tttcgtgaat gtagcttcat ttaacagcaa tgctcaggat    900
gtaagctgtt ttcagcacct tgtccaagca atgtaagaa ataaaaagt gttgaaagac       960 gcggtgaata atatcacagc caaggaatt acagattata agaagggctt tagttttgct     1020
```

-continued

```
tttgaacagc tgcttaatta taatgtttcc agagcaaact gcaataagat tattatgcta    1080
ttcacggatg gaggagaaga gagagcccag gagatattta acaaatacaa taaagataaa    1140
aaagtacgtg tattcaggtt ttcagttggt caacacaatt atgagagagg acctattcag    1200
tggatggcct gtgaaaacaa aggttattat tatgaaattc cttccattgg tgcaataaga    1260
atcaatactc aggaatattt ggatgttttg ggaagaccaa tggttttagc aggagacaaa    1320
gctaagcaag tccaatggac aaatgtgtac ctggatgcat tggaactggg acttgtcatt    1380
actggaactc ttccggtctt caacataacc ggccaatttg aaaataagac aaacttaaag    1440
aaccagctga ttcttggtgt gatgggagta gatgtgtctt tggaagatat taaaagactg    1500
acaccacgtt ttacactgtg ccccaatggg tattactttg caatcgatcc taatggttat    1560
gttttattac atccaaatct tcagccaaag aaccccaaat ctcaggagcc agtaacattg    1620
gatttccttg atgcagagtt agagaatgat attaaagtgg agattcgaaa taagatgatt    1680 gatgggaaa gtggagaaaa aacattcaga actctggtta aatctcaaga tgagagatat    1740
attgacaaag gaaacaggac atacacatgg acacctgtca atggcacaga ttacagtttg    1800
gccttggtat taccaaccta cagttttttac tatataaaag ccaaactaga agagacaata    1860
actcaggcca gatcaaaaaa gggcaaaatg aaggattcgg aaaccctgaa gccagataat    1920
tttgaagaat ctggctatac attcatagca ccaagagatt actgcaatga cctgaaaata    1980
tcggataata acactgaatt tcttttaaat ttcaacgagt ttattgatag aaaaactcca    2040
aacaacccat catgtaacgc ggatttgatt aatagagtct tgcttgatgc aggctttaca    2100
aatgaacttg tccaaaatta ctggagtaag cagaaaaata tcaagggagt gaaagcacga    2160
tttgttgtga ctgatggtgg gattaccaga gtttatccca aagaggctgg agaaaattgg    2220
caagaaaacc cagagacata tgaggacagc ttctataaaa ggagcctaga taatgataac    2280
tatgttttca ctgctcccta ctttaacaaa agtggacctg gtgcctatga atcgggcatt    2340
atggtaagca agctgtagaa atatatatt caagggaaac ttcttaaacc tgcagttgtt    2400
ggaattaaaa ttgatgtaaa ttcctggata gagaatttca ccaaaacctc aatcagagat    2460
ccgtgtgctg gtccagtttg tgactgcaaa agaaacagtg acgtaatgga ttgtgtgatt    2520
ctggatgatg gtgggtttct tctgatggca aatcatgatg attatactaa tcagattgga    2580
agattttttg gagagattga tcccagcttg atgagacacc tggttaatat atcagtttat    2640
gcttttaaca atcttatga ttatcagtca gtatgtgagc ccggtgctgc accaaaacaa    2700
ggagcaggac atcgctcagc atatgtgcca tcagtagcag acatattaca aattggctgg    2760
tgggccactg ctgctgcctg gtctattcta cagcagtttc tcttgagttt gacctttcca    2820
cgactccttg aggcagttga gatggaggat gatgacttca cggcctccct gtccaagcag    2880
agctgcatta ctgaacaaac ccagtatttc ttcgataacg acagtaaatc attcagtggt    2940
gtattagact gtgaaaactg ttccagaatc tttcatggag aaaagcttat gaacaccaac    3000
ttaatattca taatggttga gagcaaaggg acatgtccat gtgacacacg actgctcata    3060
caagcggagc agacttctga cggtccaaat ccttgtgaca tggttaagc               3109
```

<210> SEQ ID NO 12
<211> LENGTH: 3190
<212> TYPE: DNA
<213> ORGANISM: Homo sapiens

<400> SEQUENCE: 12

```
atggctgctg gctgcctgct ggccttgact ctgacacttt tccaatcttt gctcatcggc     60
```

-continued

```
ccctcgtcgg aggagccgtt cccttcggcc gtcactatca aatcatgggt ggataagatg      120
caagaagacc ttgtcacact ggcaaaaaca gcaagtggag tcaatcagct tgttgatatt      180
tatgagaaat atcaagattt gtatactgtg aaccaaata  atgcacgcca gctggtagaa      240
attgcagcca gggatattga gaaacttctg agcaacagat ctaaagccct ggtgagcctg      300
gcattggaag cggagaaagt tcaagcagct caccagtgga gagaagattt tgcaagcaat      360
gaagttgtct actacaatgc aaaggatgat ctcgatcctg agaaaatga  cagtgagcca      420 ggcagccaga ggataaaacc tgttttcatt gaagatgcta attttggacg acaaatatct      480
tatcagcacg cagcagtcca tattcctact gacatctatg agggctcaac aattgtgtta      540
aatgaactca actggacaag tgccttagat gaagttttca aaaagaatcg cgaggaagac      600
ccttcattat tgtggcaggt ttttggcagt gccactggcc tagctcgata ttatccagct      660
tcaccatggg ttgataatag tagaactcca aataagattg accttatga  tgtacgcaga      720 agaccatggt acatccaagg agctgcatct cctaaagaca tgcttattct ggtggatgtg      780
agtggaagtg ttagtggatt gacacttaaa ctgatccgaa catctgtctc cgaaatgtta      840
gaaaccctct cagatgatga tttcgtgaat gtagcttcat ttaacagcaa tgctcaggat      900
gtaagctgtt ttcagcacct tgtccaagca aatgtaagaa ataaaaaagt gttgaaagac      960
gcggtgaata atatcacagc caaaggaatt acagattata agaagggctt tagttttgct     1020
tttgaacagc tgcttaatta taatgttttcc agagcaaact gcaataagat tattatgcta     1080
ttcacggatg gaggagaaga gagagcccag gagatattta caaaatacaa taaagataaa     1140
aaagtacgtg tattcaggtt ttcagttggt caacacaatt atgagagagg acctattcag     1200
tggatggcct gtgaaaacaa aggttattat tatgaaattc cttccattgg tgcaataaga     1260
atcaatactc aggaatattt ggatgttttg ggaagaccaa tggttttagc aggagacaaa     1320
gctaagcaag tccaatggac aaatgtgtac ctggatgcat ggaactggg  acttgtcatt     1380 actggaactc ttccggtctt caacataacc ggccaatttg aaaataagac aaacttaaag     1440
aaccagctga ttcttggtgt gatgggagta gatgtgtctt ggaagatat  taaaagactg     1500 acaccacgtt ttacactgtg ccccaatggg tattactttg caatcgatcc taatggttat     1560
gttttattac atccaaatct tcagccaaag aaccccaaat ctcaggagcc agtaacattg     1620
gatttccttg atgcagagtt agagaatgat attaaagtgg agattcgaaa taagatgatt     1680 gatgggaaa  gtggagaaaa aacattcaga actctggtta aatctcaaga tgagagatat     1740
attgacaaag gaaacaggac atacacatgg acacctgtca atggcacaga ttacagtttg     1800
gccttggtat taccaaccta cagtttttac tatataaaag ccaaactaga agagacaata     1860
actcaggcca gatcaaaaaa gggcaaaatg aaggattcgg aaaccctgaa gccagataat     1920
tttgaagaat ctggctatac attcatagca ccaagagatt actgcaatga cctgaaaata     1980
tcggataata acactgaatt tcttttaaat ttcaacgagt ttattgatag aaaaactcca     2040
aacaacccat catgtaacgc ggatttgatt aatagagtct tgcttgatgc aggctttaca     2100
aatgaacttg tccaaaatta ctggagtaag cagaaaaata tcaagggagt gaaagcacga     2160
tttgttgtga ctgatggtgg gattaccaga gtttatccca aagaggctgg agaaaattgg     2220
caagaaaacc cagagacata tgaggacagc ttctataaaa ggagcctaga taatgataac     2280
tatgttttca ctgctcccta ctttaacaaa agtggacctg gtgcctatga atcgggcatt     2340
atggtaagca aagctgtaga aatatatatt caagggaaac ttcttaaacc tgcagttgtt     2400
```

-continued

```
ggaattaaaa ttgatgtaaa ttcctggata gagaatttca ccaaaacctc aatcagagat    2460
ccgtgtgctg gtccagtttg tgactgcaaa agaaacagtg acgtaatgga ttgtgtgatt    2520
ctggatgatg gtgggtttct tctgatggca aatcatgatg attatactaa tcagattgga    2580 agatttttg gagagattga tcccagcttg atgagacacc tggttaatat atcagtttat     2640
gcttttaaca aatcttatga ttatcagtca gtatgtgagc ccggtgctgc accaaaacaa    2700
ggagcaggac atcgctcagc atatgtgcca tcagtagcag acatattaca aattggctgg    2760
tgggccactg ctgctgcctg gtctattcta cagcagtttc tcttgagttt gacctttcca    2820
cgactccttg aggcagttga gatggaggat gatgacttca cggcctccct gtccaagcag    2880
agctgcatta ctgaacaaac ccagtatttc ttcgataacg acagtaaatc attcagtggt    2940
gtattagact gtgaaactg ttccagaatc tttcatggaa aaagcttat gaacaccaac      3000 ttaatattca taatggttga gagcaaaggg acatgtccat gtgacacacg actgctcata    3060
caagcggagc agacttctga cggtccaaat ccttgtgaca tggttaagca acctagatac    3120
cgaaaagggc ctgatgtctg ctttgataac aatgtcttgg aggattatac tgactgtggt    3180
ggtgtttctg                                                           3190
```

<210> SEQ ID NO 13
<211> LENGTH: 1018
<212> TYPE: PRT
<213> ORGANISM: Homo sapiens

<400> SEQUENCE: 13

```
Met Ala Ala Gly Cys Leu Leu Ala Leu Thr Leu Thr Leu Phe Gln Ser
  1               5                  10                  15

Leu Leu Ile Gly Pro Ser Ser Glu Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
```

```
                225                 230                 235                 240
Arg Pro Trp Tyr Ile Gln Gly Ala Ala Ser Pro Lys Asp Met Leu Ile
                245                 250                 255
Leu Val Asp Val Ser Gly Ser Val Ser Gly Leu Thr Leu Lys Leu Ile
                260                 265                 270
Arg Thr Ser Val Ser Glu Met Leu Glu Thr Leu Ser Asp Asp Asp Phe
                275                 280                 285
Val Asn Val Ala Ser Phe Asn Ser Asn Ala Gln Asp Val Ser Cys Phe
                290                 295                 300
Gln His Leu Val Gln Ala Asn Val Arg Asn Lys Lys Val Leu Lys Asp
305                 310                 315                 320
Ala Val Asn Asn Ile Thr Ala Lys Gly Ile Thr Asp Tyr Lys Lys Gly
                325                 330                 335
Phe Ser Phe Ala Phe Glu Gln Leu Leu Asn Tyr Asn Val Ser Arg Ala
                340                 345                 350
Asn Cys Asn Lys Ile Ile Met Leu Phe Thr Asp Gly Gly Glu Glu Arg
                355                 360                 365
Ala Gln Glu Ile Phe Asn Lys Tyr Asn Lys Asp Lys Lys Val Arg Val
370                 375                 380
Phe Arg Phe Ser Val Gly Gln His Asn Tyr Glu Arg Gly Pro Ile Gln
385                 390                 395                 400
Trp Met Ala Cys Glu Asn Lys Gly Tyr Tyr Tyr Glu Ile Pro Ser Ile
                405                 410                 415
Gly Ala Ile Arg Ile Asn Thr Gln Glu Tyr Leu Asp Val Leu Gly Arg
                420                 425                 430
Pro Met Val Leu Ala Gly Asp Lys Ala Lys Gln Val Gln Trp Thr Asn
                435                 440                 445
Val Tyr Leu Asp Ala Leu Glu Leu Gly Leu Val Ile Thr Gly Thr Leu
                450                 455                 460
Pro Val Phe Asn Ile Thr Gly Gln Phe Glu Asn Lys Thr Asn Leu Lys
465                 470                 475                 480
Asn Gln Leu Ile Leu Gly Val Met Gly Val Asp Val Ser Leu Glu Asp
                485                 490                 495
Ile Lys Arg Leu Thr Pro Arg Phe Thr Leu Cys Pro Asn Gly Tyr Tyr
                500                 505                 510
Phe Ala Ile Asp Pro Asn Gly Tyr Val Leu Leu His Pro Asn Leu Gln
                515                 520                 525
Pro Lys Asn Pro Lys Ser Gln Glu Pro Val Thr Leu Asp Phe Leu Asp
                530                 535                 540
Ala Glu Leu Glu Asn Asp Ile Lys Val Glu Ile Arg Asn Lys Met Ile
545                 550                 555                 560
Asp Gly Glu Ser Gly Glu Lys Thr Phe Arg Thr Leu Val Lys Ser Gln
                565                 570                 575
Asp Glu Arg Tyr Ile Asp Lys Gly Asn Arg Thr Tyr Thr Trp Thr Pro
                580                 585                 590
Val Asn Gly Thr Asp Tyr Ser Leu Ala Leu Val Leu Pro Thr Tyr Ser
                595                 600                 605
Phe Tyr Tyr Ile Lys Ala Lys Leu Glu Glu Thr Ile Thr Gln Ala Arg
                610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
                645                 650                 655
```

```
Asp Leu Lys Ile Ser Asp Asn Asn Thr Glu Phe Leu Leu Asn Phe Asn
            660                 665                 670
Glu Phe Ile Asp Arg Lys Thr Pro Asn Asn Pro Ser Cys Asn Ala Asp
            675                 680                 685
Leu Ile Asn Arg Val Leu Leu Asp Ala Gly Phe Thr Asn Glu Leu Val
            690                 695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
            755                 760                 765
Asn Lys Ser Gly Pro Gly Ala Tyr Glu Ser Gly Ile Met Val Ser Lys
            770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
            820                 825                 830
Ser Asp Val Met Asp Cys Val Ile Leu Asp Asp Gly Gly Phe Leu Leu
            835                 840                 845
Met Ala Asn His Asp Asp Tyr Thr Asn Gln Ile Gly Arg Phe Phe Gly
850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Val
            900                 905                 910
Ala Asp Ile Leu Gln Ile Gly Trp Trp Ala Thr Ala Ala Ala Trp Ser
            915                 920                 925
Ile Leu Gln Gln Phe Leu Leu Ser Leu Thr Phe Pro Arg Leu Leu Glu
            930                 935                 940
Ala Val Glu Met Glu Asp Asp Asp Phe Thr Ala Ser Leu Ser Lys Gln
945                 950                 955                 960
Ser Cys Ile Thr Glu Gln Thr Gln Tyr Phe Phe Asp Asn Asp Ser Lys
                965                 970                 975
Ser Phe Ser Gly Val Leu Asp Cys Gly Asn Cys Ser Arg Ile Phe His
            980                 985                 990
Gly Glu Lys Leu Met Asn Thr Asn Leu Ile Phe Ile Met Val Glu Ser
            995                1000                1005
Lys Gly Thr Cys Pro Cys Asp Thr Arg Leu
   1010                1015

<210> SEQ ID NO 14
<211> LENGTH: 1036
<212> TYPE: PRT
<213> ORGANISM: Homo sapiens

<400> SEQUENCE: 14

Met Ala Ala Gly Cys Leu Leu Ala Leu Thr Leu Thr Leu Phe Gln Ser
```

-continued

```
  1               5              10              15
Leu Leu Ile Gly Pro Ser Ser Glu Glu Pro Phe Pro Ser Ala Val Thr
             20                  25                  30
Ile Lys Ser Trp Val Asp Lys Met Gln Glu Asp Leu Val Thr Leu Ala
             35                  40                  45
Lys Thr Ala Ser Gly Val Asn Gln Leu Val Asp Ile Tyr Glu Lys Tyr
 50                  55                  60
Gln Asp Leu Tyr Thr Val Glu Pro Asn Asn Ala Arg Gln Leu Val Glu
 65                  70                  75                  80
Ile Ala Ala Arg Asp Ile Glu Lys Leu Leu Ser Asn Arg Ser Lys Ala
                 85                  90                  95
Leu Val Ser Leu Ala Leu Glu Ala Glu Lys Val Gln Ala Ala His Gln
                100                 105                 110
Trp Arg Glu Asp Phe Ala Ser Asn Glu Val Val Tyr Tyr Asn Ala Lys
                115                 120                 125
Asp Asp Leu Asp Pro Glu Lys Asn Asp Ser Glu Pro Gly Ser Gln Arg
            130                 135                 140
Ile Lys Pro Val Phe Ile Glu Asp Ala Asn Phe Gly Arg Gln Ile Ser
145                 150                 155                 160
Tyr Gln His Ala Ala Val His Ile Pro Thr Asp Ile Tyr Glu Gly Ser
                165                 170                 175
Thr Ile Val Leu Asn Glu Leu Asn Trp Thr Ser Ala Leu Asp Glu Val
                180                 185                 190
Phe Lys Lys Asn Arg Glu Glu Asp Pro Ser Leu Leu Trp Gln Val Phe
            195                 200                 205
Gly Ser Ala Thr Gly Leu Ala Arg Tyr Tyr Pro Ala Ser Pro Trp Val
            210                 215                 220
Asp Asn Ser Arg Thr Pro Asn Lys Ile Asp Leu Tyr Asp Val Arg Arg
225                 230                 235                 240
Arg Pro Trp Tyr Ile Gln Gly Ala Ala Ser Pro Lys Asp Met Leu Ile
                245                 250                 255
Leu Val Asp Val Ser Gly Ser Val Ser Gly Leu Thr Leu Lys Leu Ile
                260                 265                 270
Arg Thr Ser Val Ser Glu Met Leu Glu Thr Leu Ser Asp Asp Asp Phe
            275                 280                 285
Val Asn Val Ala Ser Phe Asn Ser Asn Ala Gln Asp Val Ser Cys Phe
            290                 295                 300
Gln His Leu Val Gln Ala Asn Val Arg Asn Lys Lys Val Leu Lys Asp
305                 310                 315                 320
Ala Val Asn Asn Ile Thr Ala Lys Gly Ile Thr Asp Tyr Lys Lys Gly
                325                 330                 335
Phe Ser Phe Ala Phe Glu Gln Leu Leu Asn Tyr Asn Val Ser Arg Ala
            340                 345                 350
Asn Cys Asn Lys Ile Ile Met Leu Phe Thr Asp Gly Gly Glu Glu Arg
            355                 360                 365
Ala Gln Glu Ile Phe Asn Lys Tyr Asn Lys Asp Lys Lys Val Arg Val
        370                 375                 380
Phe Arg Phe Ser Val Gly Gln His Asn Tyr Glu Arg Gly Pro Ile Gln
385                 390                 395                 400
Trp Met Ala Cys Glu Asn Lys Gly Tyr Tyr Tyr Glu Ile Pro Ser Ile
                405                 410                 415
Gly Ala Ile Arg Ile Asn Thr Gln Glu Tyr Leu Asp Val Leu Gly Arg
            420                 425                 430
```

-continued

```
Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
        450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
        610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Ala Asp
        675                 680                 685

Leu Ile Asn Arg Val Leu Leu Asp Ala Gly Phe Thr Asn Glu Leu Val
        690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
        770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
        835                 840                 845
```

Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
            900                 905                 910

Ala Asp Ile Leu Gln Ile Gly Trp Trp Ala Thr Ala Ala Trp Ser
            915                 920                 925

Ile Leu Gln Gln Phe Leu Leu Ser Leu Thr Phe Pro Arg Leu Leu Glu
    930                 935                 940

Ala Val Glu Met Glu Asp Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys
1025                1030                1035

<210> SEQ ID NO 15
<211> LENGTH: 1063
<212> TYPE: PRT
<213> ORGANISM: Homo sapiens

<400> SEQUENCE: 15

Met Ala Ala Gly Cys Leu Leu Ala Leu Thr Leu Thr Leu Phe Gln Ser
1               5                   10                  15

Leu Leu Ile Gly Pro Ser Ser Glu Glu Pro Phe Pro Ser Ala Val Thr
                20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
        50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
                100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
        130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
                180                 185                 190

```
Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
                260                 265                 270

Arg Thr Ser Val Ser Glu Met Leu Glu Thr Leu Ser Asp Asp Asp Phe
            275                 280                 285

Val Asn Val Ala Ser Phe Asn Ser Asn Ala Gln Asp Val Ser Cys Phe
        290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
                340                 345                 350

Asn Cys Asn Lys Ile Ile Met Leu Phe Thr Asp Gly Gly Glu Glu Arg
            355                 360                 365

Ala Gln Glu Ile Phe Asn Lys Tyr Asn Lys Asp Lys Lys Val Arg Val
        370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
        450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
            515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
            595                 600                 605
```

-continued

```
Phe Tyr Tyr Ile Lys Ala Lys Leu Glu Glu Thr Ile Thr Gln Ala Arg
    610             615                 620

Ser Lys Lys Gly Lys Met Lys Asp Ser Glu Thr Leu Lys Pro Asp Asn
625             630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
                660                 665                 670

Glu Phe Ile Asp Arg Lys Thr Pro Asn Asn Pro Ser Cys Asn Ala Asp
            675                 680                 685

Leu Ile Asn Arg Val Leu Leu Asp Ala Gly Phe Thr Asn Glu Leu Val
        690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
                740                 745                 750

Lys Arg Ser Leu Asp Asn Asp Asn Tyr Val Phe Thr Ala Pro Tyr Phe
            755                 760                 765

Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
            885                 890                 895

Ala Pro Lys Gln Gly Ala Gly His Arg Ser Ala Tyr Val Pro Ser Val
            900                 905                 910

Ala Asp Ile Leu Gln Ile Gly Trp Trp Ala Thr Ala Ala Ala Trp Ser
        915                 920                 925

Ile Leu Gln Gln Phe Leu Leu Ser Leu Thr Phe Pro Arg Leu Leu Glu
    930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
                980                 985                 990

Gly Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys Gln Pro Arg Tyr
```

-continued

```
1025                1030                1035                1040
Arg Lys Gly Pro Asp Val Cys Phe Asp Asn Asn Val Leu Glu Asp Tyr
                1045                1050                1055

Thr Asp Cys Gly Gly Val Ser
            1060

<210> SEQ ID NO 16
<211> LENGTH: 1091
<212> TYPE: PRT
<213> ORGANISM: Homo sapiens

<400> SEQUENCE: 16

Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
                20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
 50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
                100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
 130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
                180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
 210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
                260                 265                 270

Arg Thr Ser Val Ser Glu Met Leu Glu Thr Leu Ser Asp Asp Asp Phe
            275                 280                 285

Val Asn Val Ala Ser Phe Asn Ser Asn Ala Gln Asp Val Ser Cys Phe
 290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335
```

-continued

```
Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
                580                 585                 590

Val Asn Gly Thr Asp Tyr Ser Leu Ala Leu Val Leu Pro Thr Tyr Ser
                595                 600                 605

Phe Tyr Tyr Ile Lys Ala Lys Leu Glu Glu Thr Ile Thr Gln Ala Arg
            610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Ala Asp
        675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
```

-continued

```
                755                  760                 765
Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
                820                 825                 830

Ser Asp Val Met Asp Cys Val Ile Leu Asp Asp Gly Gly Phe Leu Leu
                835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
                900                 905                 910

Ala Asp Ile Leu Gln Ile Gly Trp Trp Ala Thr Ala Ala Trp Ser
                915                 920                 925

Ile Leu Gln Gln Phe Leu Leu Ser Leu Thr Phe Pro Arg Leu Leu Glu
930                 935                 940

Ala Val Glu Met Glu Asp Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
                980                 985                 990

Gly Glu Lys Leu Met Asn Thr Asn Leu Ile Phe Ile Met Val Glu Ser
                995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys Gln Pro Arg Tyr
1025                1030                1035                1040

Arg Lys Gly Pro Asp Val Cys Phe Asp Asn Asn Val Leu Glu Asp Tyr
                1045                1050                1055

Thr Asp Cys Gly Gly Val Ser Gly Leu Asn Pro Ser Leu Trp Tyr Ile
                1060                1065                1070

Ile Gly Ile Gln Phe Leu Leu Leu Trp Leu Val Ser Gly Ser Thr His
        1075                1080                1085

Arg Leu Leu
    1090
```

<210> SEQ ID NO 17
<211> LENGTH: 3600
<212> TYPE: DNA
<213> ORGANISM: Homo sapiens

<400> SEQUENCE: 17

```
gcgggggagg gggcattgat cttcgatcgc gaagatggct gctggctgcc tgctggcctt      60
gactctgaca cttttccaat ctttgctcat cggcccctcg tcggaggagc cgttcccttc     120
ggccgtcact atcaaatcat gggtggataa gatgcaagaa gaccttgtca cactggcaaa    180
```

```
aacagcaagt ggagtcaatc agcttgttga tatttatgag aaatatcaag atttgtatac    240
tgtggaacca aataatgcac gccagctggt agaaattgca gccagggata ttgagaaact    300
tctgagcaac agatctaaag ccctggtgag cctggcattg gaagcggaga agttcaagc    360 agctcaccag tggagagaag attttgcaag caatgaagtt gtctactaca atgcaaagga    420
tgatctcgat cctgagaaaa atgacagtga gccaggcagc cagaggataa aacctgtttt    480
cattgaagat gctaattttg gacgacaaat atcttatcag cacgcagcag tccatattcc    540
tactgacatc tatgagggct caacaattgt gttaaatgaa ctcaactgga caagtgcctt    600
agatgaagtt ttcaaaaaga atcgcgagga agacccttca ttattgtggc aggttttgg    660 cagtgccact ggcctagctc gatattatcc agcttcacca tgggttgata atagtagaac    720
tccaaataag attgaccttt atgatgtacg cagaagacca tggtacatcc aaggagctgc    780
atctcctaaa gacatgctta ttctggtgga tgtgagtgga agtgttagtg gattgacact    840
taaactgatc cgaacatctg tctccgaaat gttagaaacc ctctcagatg atgatttcgt    900
gaatgtagct tcatttaaca gcaatgctca ggatgtaagc tgttttcagc accttgtcca    960
agcaaatgta agaaataaaa aagtgttgaa agacgcggtg aataatatca cagccaaagg   1020
aattacagat tataagaagg ctttagtttt tgcttttgaa cagctgctta attataatgt   1080
tccagagcaa aactgcaata agattattat gctattcacg gatggaggag aagagagagc   1140
ccaggagata tttaacaaat acaataaaga taaaaagta cgtgtattca ggttttcagt   1200
tggtcaacac aattatgaga gaggacctat tcagtggatg gcctgtgaaa acaaaggtta   1260
ttattatgaa attccttcca ttggtgcaat aagaatcaat actcaggaat atttggatgt   1320
tttgggaaga ccaatggttt tagcaggaga caaagctaag caagtccaat ggacaaatgt   1380
gtacctggat gcattggaac tgggacttgt cattactgga actcttccgg tcttcaacat   1440
aaccggccaa tttgaaaata agacaaactt aagaaccag ctgattcttg gtgtgatggg   1500
agtagatgtg tctttggaag atattaaaag actgacacca cgttttacac tgtgccccaa   1560
tgggtattac tttgcaatcg atcctaatgg ttatgtttta ttcatccaa atcttcagcc   1620 aaagaacccc aaatctcagg agccagtaac attggatttc cttgatgcag agttagagaa   1680
tgatattaaa gtggagattc gaaataagat gattgatggg gaaagtggag aaaaaacatt   1740
cagaactctg gttaaatctc aagatgagag atatattgac aaaggaaaca ggacatacac   1800
atggacacct gtcaatggca cagattacag ttttggcctt g gtattaccaa cctacagttt   1860
ttactatata aaagccaaac tagaagagac aataactcag gccagatcaa aaaagggcaa   1920
aatgaaggat tcggaaaccc tgaagccaga taattttgaa gaatctggct atacattcat   1980
agcaccaaga gattactgca atgacctgaa atatcggat aataacactg aattttcttttt   2040 aaatttcaac gagtttattg atagaaaaac tccaaacaac ccatcatgta acgcggattt   2100
gattaataga gtcttgcttg atgcaggctt tacaaatgaa cttgtccaaa attactggag   2160
taagcagaaa aatatcaagg gagtgaaagc acgatttgtt gtgactgatg gtgggattac   2220
cagagtttat cccaaagagg ctggagaaaa ttggcaagaa aacccagaga catatgagga   2280
cagcttctat aaaaggagcc tagataatga taactatgtt ttcactgctc cctactttaa   2340
caaaagtgga cctggtgcct atgaatcggg cattatggta agcaaagctg tagaaatata   2400
tattcaaggg aaacttctta aacctgcagt tgttggaatt aaaattgatg taaattcctg   2460
gatagagaat ttcaccaaaa cctcaatcag agatccgtgt gctggtccag tttgtgactg   2520
caaaagaaac agtgacgtaa tggattgtgt gattctggat gatggtgggt tcttctgat    2580
```

```
ggcaaatcat gatgattata ctaatcagat tggaagattt tttggagaga ttgatcccag    2640
cttgatgaga cacctggtta atatatcagt ttatgctttt aacaaatctt atgattatca    2700
gtcagtatgt gagcccggtg ctgcaccaaa acaaggagca ggacatcgct cagcatatgt    2760
gccatcagta gcagacatat tacaaattgg ctggtgggcc actgctgctg cctggtctat    2820
tctacagcag tttctcttga gtttgacctt tccacgactc cttgaggcag ttgagatgga    2880
ggatgatgac ttcacggcct ccctgtccaa gcagagctgc attactgaac aaacccagta    2940
tttcttcgat aacgacagta aatcattcag tggtgtatta gactgtggaa actgttccag    3000
aatctttcat ggagaaaagc ttatgaacac caacttaata ttcataatgg ttgagagcaa    3060
agggacatgt ccatgtgaca cacgactgct catacaagcg gagcagactt ctgacggtcc    3120
aaatccttgt gacatggtta agcaacctag ataccgaaaa gggcctgatg tctgctttga    3180
taacaatgtc ttggaggatt atactgactg tggtggtgtt tctggattaa atccctccct    3240
gtggtatatc attggaatcc agtttctact actttggctg gtatctggca gcacacaccg    3300
gctgttatga ccttctaaaa accaaatctg catagttaaa ctccagaccc tgccaaaaca    3360
tgagccctgc cctcaattac agtaacgtag ggtcagctat aaaatcagac aaacattagc    3420
tgggcctgtt ccatggcata acactaaggc gcagactcct aaggcaccca ctggctgcat    3480
gtcagggtgt cagatcctta aacgtgtgtg aatgctgcat catctatgtg taacatcaaa    3540
gcaaaatcct atacgtgtcc tctattggaa aatttgggcg tttgttgttg cattgttggt    3600
```

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 18
ggggattgat cttcgatcgc g                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 19
ctgagatttg gggttctttg g                                              21

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 20
tcgccaccat ggctgctggc tgcctgctg                                      29

<210> SEQ ID NO 21
<211> LENGTH: 52
<212> TYPE: DNA

-continued

```
<213> ORGANISM: Artificial Sequence
<220> FEATURE:
<223> OTHER INFORMATION: Description of Artificial Sequence: primer

<400> SEQUENCE: 21
tcggaattcc tcagtgatgg tgatggtgat gagaaacacc accacagtcg gt          52
```